United States Patent
Arab

(10) Patent No.: US 11,268,135 B2
(45) Date of Patent: Mar. 8, 2022

(54) COMPOSITIONS AND METHODS FOR IDENTIFYING, QUANTIFYING, AND/OR CHARACTERIZING AN ANALYTE

(71) Applicant: PATTERN BIOSCIENCE, INC., Austin, TX (US)

(72) Inventor: Nicolas Arab, Austin, TX (US)

(73) Assignee: PATTERN BIOSCIENCE, INC., Austin, TX (US)

(*) Notice: Subject to any disclaimer, the term of this patent is extended or adjusted under 35 U.S.C. 154(b) by 282 days.

(21) Appl. No.: 16/300,469

(22) PCT Filed: May 10, 2017

(86) PCT No.: PCT/IB2017/052745
§ 371 (c)(1),
(2) Date: Nov. 9, 2018

(87) PCT Pub. No.: WO2017/195137
PCT Pub. Date: Nov. 16, 2017

(65) Prior Publication Data
US 2019/0144925 A1  May 16, 2019

Related U.S. Application Data

(60) Provisional application No. 62/334,191, filed on May 10, 2016.

(51) Int. Cl.
C12Q 1/6818  (2018.01)
G01N 33/542  (2006.01)
C12Q 1/68    (2018.01)

(52) U.S. Cl.
CPC ............ C12Q 1/6818 (2013.01); C12Q 1/68 (2013.01); G01N 33/542 (2013.01)

(58) Field of Classification Search
CPC ........ C12Q 2521/345; C12Q 2563/125; C12Q 1/682; C12Q 2537/149; C12Q 2537/155; C12Q 2565/101; C12Q 2565/1015
See application file for complete search history.

(56) References Cited

U.S. PATENT DOCUMENTS 5,475,096 A   12/1995  Gold et al.
5,595,877 A   1/1997   Gold et al.
(Continued)

FOREIGN PATENT DOCUMENTS

WO  WO 2003/025113   3/2003
WO  WO 2013/130875   9/2013
(Continued)

OTHER PUBLICATIONS

Gruner et al. Stabilisers for water-in-fluorinated-oil dispersions: Key properties for microfluidic applications. Current Opinion in Colloid & Interface Science 20:183-191. (Year: 2015).*
(Continued)

Primary Examiner — Samuel C Woolwine
(74) Attorney, Agent, or Firm — Norton Rose Fulbright US LLP

(57) ABSTRACT

Embodiments of this invention are directed towards the sensitive, fast, and accurate identification and/or characterization of a single cell or bacterium, particularly phenotypic characterization. Certain aspects of the invention include assays that include functional nucleic acid probes (FNAPs). FNAPs can be used to generate deoxyribozyme cleavage cascades (DRCC) initiated by activation of a FNAP resulting in a detectable signal from a single cell.

20 Claims, 12 Drawing Sheets
Specification includes a Sequence Listing.

(56) References Cited

U.S. PATENT DOCUMENTS

| | | | |
|---|---|---|---|
| 5,660,985 | A | 8/1997 | Pieken et al. |
| 6,180,348 | B1 | 1/2001 | Li |
| 6,673,578 | B1 | 1/2004 | Uemori et al. |
| 6,990,290 | B2 | 1/2006 | Kylberg et al. |
| 2002/0187484 | A1 | 12/2002 | Thorson et al. |
| 2005/0084923 | A1 | 4/2005 | Mueller et al. |
| 2007/0231810 | A1 | 10/2007 | Todd et al. |
| 2007/0254282 | A1 | 11/2007 | Willner et al. |
| 2009/0087838 | A1 | 4/2009 | Reif et al. |
| 2010/0227767 | A1 | 9/2010 | Boedicker et al. |
| 2019/0218497 | A1 | 7/2019 | Boedicker et al. |

FOREIGN PATENT DOCUMENTS

| | | |
|---|---|---|
| WO | WO 2014/145555 | 9/2014 |
| WO | WO 2015/048173 | 4/2015 |

OTHER PUBLICATIONS

Tan et al. Monodispersed microfluidic droplet generation by shear focusing microfluidic device. Sensors and Actuators B 114:350-356. (Year: 2006).*

Cairns et al., "Optimisation of the 10-23 DNAzyme-substrate pairing enhanced RNA cleavage activity at purine-cytosine target sites" *Nucleic Acids Research*, 2003, 31(11):2883-2889.

International Search Report and Written Opinion issued in International Patent Application No. PCT/IB2017/052745, dated Aug. 16, 2017.

Joyce, "RNA cleavage by the 10-23 DNA enzyme" *Methods, Enzymol.*, 2001, 341:503-517.

Shi et al., "Activatable aptamer probe for contrast-enhanced in vivo cancer imaging based on cell membrane protein-triggered conformation alteration" *PNAS*, 2011, 108(10):3900.

Simon et al., "A Laplace pressure based microfluidic trap for passive droplet trapping nd controlled release," *Biomicrofluidics*, 2012, 6:014110.

Zhang et al., "Control of DNA Strand Displacement Kinetics Using Toehold Exchange" *J. Am. Chem. Soc.*, 2009, 131:17303-17314.

U.S. Appl. No. 60/962,426, filed Jul. 26, 2007, Boedicker, et al.

U.S. Appl. No. 61/052,490, filed May 12, 2008, Boedicker, et al.

* cited by examiner

Probe S
```
     6      1     1'      CC           2       8Y    1    1'     5        1[1:6]'  6'
    GCG CAGAAACC A GGCTAGCTACAACGA ATACCTCAGA GrU CAGAAACC A AAAAAAAAAAAC TTTCTG CGC
```
SEQ ID NO:3

SEQ ID NO:3

Probe P
```
 Y      1'      Y'         CC               2'       R
rU GGTTTCTGA GGCTAGCTACAACGA TCTGAGGTAT G
```
SEQ ID NO:4
FIG. 11
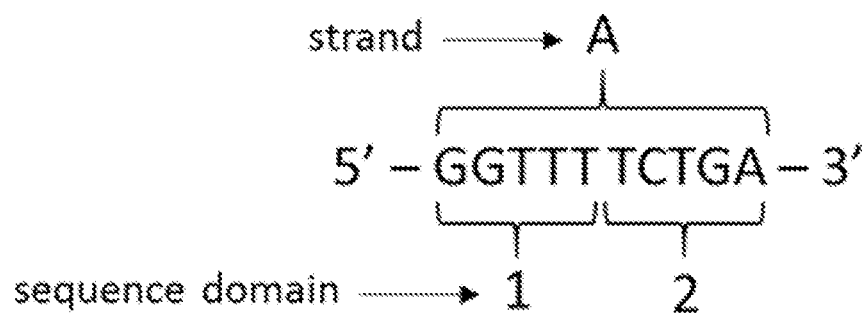
FIG. 12
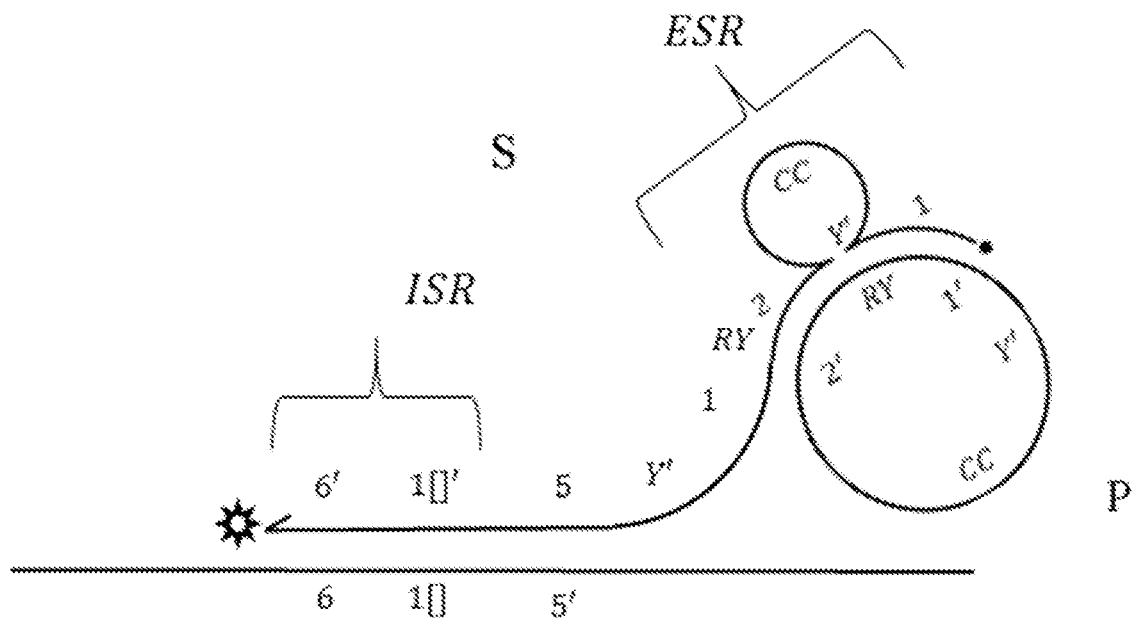
Target recognition sequence
FIG. 13

Probe S

Allosteric site (target recognition)

```
  6     1      Y'       CC              2       RY    1    Y'   5           1[1:6]'  6'
GCG CAGAAACC A GGCTAGCTACAACGA ATACCTCAGA GrU CAGAAACC A CCACACCATAC TTTCTGCG C
```
SEQ ID NO:5

Target (miRNA mimic)
GCGCAGAAAGUAUGGUGUGGU     SEQ ID NO:6

Tm = 64.4 °C

SEQ ID NO:5

SEQUENCE LISTING

```
<160> NUMBER OF SEQ ID NOS: 7

<210> SEQ ID NO 1
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 1
cgccagaaac caggctagct acaacgaata cctcagaguc agaaaccaaa aaaaaaactt    60
tctgcgc                                                              67

<210> SEQ ID NO 2
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 2
```

```
ggtttctgag gctagctaca acgatctgag gtatgu                                36

<210> SEQ ID NO 3
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 3
gcgcagaaac caggctagct acaacgaata cctcagaguc agaaaccaaa aaaaaaactt      60
tctgcgc                                                               67

<210> SEQ ID NO 4
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 4
uggtttctga ggctagctac aacgatctga ggtatg                                36

<210> SEQ ID NO 5
<211> LENGTH: 68
<212> TYPE: DNA
<213> ORGANISM: Artificial Sequence
<220> FEATURE:
<223> OTHER INFORMATION: synthetic oligonucleotide

<400> SEQUENCE: 5
gcgcagaaac caggctagct acaacgaata cctcagaguc agaaaccacc acaccatact      60
ttctgcgc                                                              68

<210> SEQ ID NO 6
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 6
gcgcagaaag uauggugugg u                                                21

<210> SEQ ID NO 7
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 7
tctaaccgag gctagctaca acgaatacct cagaaaaaaa aaaaaaaact gcgccgccgg      60
gaaaatactc ggttaga                                                    77
```

COMPOSITIONS AND METHODS FOR IDENTIFYING, QUANTIFYING, AND/OR CHARACTERIZING AN ANALYTE

PRIORITY PARAGRAPH

This Application is a national phase application under 35 U.S.C. § 371 of International Application No. PCT/IB2017/052745, filed May 10, 2017, which claims the benefit of U.S. Provisional Application Ser. No. 62/334,191, filed May 10, 2016, each of which is incorporate herein by reference in their entirety.

TECHNICAL FIELD

This disclosure relates generally to molecular biology and more particularly to compositions and methods for identifying, quantifying, and/or characterizing an analyte; including functional nucleic acid probes (FNAPs) that when activated can cleave a substrate, initiating a cleavage cascade that results in a detectable signal.

BACKGROUND

Multicellular masses or mixtures, such as infections, bacterial aggregates, biofilms, tissues, and tumors, may comprise a heterogeneous cellular milieu. These complex cellular environments may often display multiple phenotypes, which may be indicative of multiple genotypes. Distilling multicellular complexity down to single cell variability is an important facet of understanding multicellular heterogeneity. In some applications, notably in infectious disease diagnosis/treatment and cancer diagnosis/treatment, the characteristic response of individual cells is important since a minority characteristic (the characteristic response of a minority of cells within the total population) can quickly become the majority characteristic under the selective pressure of treatment. For example, most tumors are heterogeneous and can evolve drug resistance since treatment applies selective pressure that promotes the growth of drug-resistant cells. Similarly, bacterial infections treated by antimicrobials produce drug resistant bacteria since only those resistant bacteria can survive and thrive with reduced competition for resources. Therefore, it is important to understand the relevant heterogeneities, particularly those that are indicative of effective treatments, within the population of target cells in a sample, necessitating analysis at the single cell level across the population. Furthermore, because it identifies effective treatments, this analysis must be performed quickly, particularly when treating a bacterial infection. Thus, single cell analysis can be important in the development of therapeutic regimens to combat diseases with multiple genotypes, in particular resistance genotypes.

Thus, single-cell analysis avoids the loss of information associated with ensemble averaging. Recently, several researchers have reported on methods that can quantify specific proteins inside a single cell via means of integrated fluorescence and in one instance with spatial resolution. These approaches are limited to those special cases where the environment of the cell does not cause changes in the fluorescence of the reporter molecule and where quenching and endogenous fluorescence do not interfere with the measurements. Moreover, these techniques restrict viewing to one or perhaps a few species at a time. Low-copy-number proteins (present at less than a few thousand molecules per cell), as well as low-copy number nucleic acids, play an important role in cell functioning, including signaling and the regulation of gene expression. Without amplification procedures, their abundance is far below the sensitivity limits of conventional protein or nucleic acid analysis methods, such as ELISA and mass spectroscopy.

Detection of analytes such as nucleic acids is one of the cornerstones of biotechnology and molecular biology. Knowledge about the presence, location, regulation, and abundance of a gene or gene product yields information critical to the diagnosis and treatment of a variety of diseases. Nucleic acid probes are typically short nucleic acid sequences used to detect, amplify, and quantify DNA and RNA for diagnostic and therapeutic applications. They are designed to specifically hybridize with particular complementary target nucleic acid sequences. Nucleic acid probes are labeled with radioactive or fluorescent tags in order to detect the presence or absence of the target nucleic acid sequence using a variety of techniques (e.g., fluorescent in-situ hybridization, Southern blot, Northern blot, and chromatography). While these techniques are useful for detecting the presence or absence of particular target sequences, their sensitivity depends on the amount of target nucleic acid present in the sample. Furthermore, living cells cannot be analyzed using these techniques since samples must be extracted, and fixed or frozen prior to analysis.

Some of the existing nucleic acid PCR-based tests (NATs) require complicated sample preparation steps which usually include lysis followed by multiple wash steps that remove inhibitory lysis reagents from the sample. In applications where the target analyte includes cellular DNA, cell lysis creates an asymmetry in the type of cells that can be efficiently detected. Mycobacteria and fungi, for example, possess a very thick cell wall compared to gram-negative bacteria or cancer cells and thus are far more difficult to detect at low concentrations without a mechanical lysis step to efficiently disrupt their cell wall. In addition, because cells are killed and disintegrated during lysis, they are not available for phenotypic characterization, such as antibiotic sensitivity or chemo-sensitivity testing. These methods must therefore rely on genotypic biomarkers to predict phenotype or drug resistance, which often portray an inaccurate or incomplete picture of the pathogens phenotypic response. For example, methicillin-resistant *Staphylococcus aureus* (MRSA) often do not express the drug resistance conferring mecA gene. In the case of gram-negative bacteria and mycobacteria, there are hundreds of loci that provide information regarding resistance but PCR-based tests can only interrogate a few loci within a single sample.

Molecular beacons are functional single-stranded DNA probes that can report the presence of specific nucleic acids. Molecular beacons are stem-loop shaped molecules containing a nucleotide sequence in the loop portion of the molecule complementary to a target DNA or RNA. Molecular beacons are labeled on one end with a fluorescent molecule and on the other with a quenching molecule. In its native hairpin structure, the quenching molecule is in close proximity with the fluorescent molecule and absorbs the light emission of the fluorescent molecule. When the complementary nucleotide sequence on the molecular beacon loop binds its target molecule, the molecular beacon undergoes a conformational change that opens up the stem-loop structure and causes the fluorescent molecule and the quenching molecule to move away from each other. The light emission from the fluorescent molecule is no longer quenched and the signal can be detected. Molecular beacons are of limited use in generating amplified signals. The fluorescent signal of a molecular beacon is an integral part of the molecular beacon. Thus, the fluorescent molecule of the molecular beacon can generate only one signal in the presence of its target. The signal cannot be further amplified or altered by use of, for example, secondary labeled antibodies.

It should be appreciated that there is a need for highly sensitive, functional nucleic acid probes capable of being activated by binding a target without being subject to foregoing limitations.

SUMMARY

Solutions to the problems relating to diagnosing and identifying effective treatments as discussed above are addressed by various aspects of the current invention. Embodiments of this invention are directed towards compositions and methods for the sensitive, fast, and accurate identification and/or characterization of an analyte, a single cell, and/or a bacterium.

Certain aspects of the invention include assays that include functional nucleic acid probes (FNAPs). Functional nucleic acids are nucleic acids that can, for example, catalyze reactions or bind specifically to particular targets or analytes. The three-dimensional structure of functional nucleic acids provides the specificity necessary to bind analytes much like the three-dimensional structure of an enzyme determines its specificity for a substrate. The small size, specificity, and ease of manipulation of nucleic acids can now be applied to functions traditionally associated with proteins (e.g., catalysis, receptors, and antibodies). FNAPs of the current invention can include those FNAPs that are allosterically, enzymatically, and allosterically and enzymatically activated. One or more FNAPs can be used to generate deoxyribozyme cleavage cascades (DRCC) that can be initiated by activation of a FNAP resulting in a detectable signal from a single cell. Activation of a FNAP can be via interaction of a binding element with its target analyte. In certain non-limiting aspects DRCC can be, but need not be, initiated in a confined volume.

Embodiments of the invention offer several advantages over existing methods. In certain aspects of the current invention cellular or bacterial surface biomarkers/targets or secreted biomarkers/targets are used for identification of a cell or bacterium, thus cell lysis is not required. Another advantage is that biomarkers are available for all cellular or bacterial targets, enabling the technique to be equally effective across cell types and pathogen species. In addition, many surface biomarkers are present in sufficient numbers, some in the tens of thousands, so there is natural amplification for a target cell compared to a single genome target per cell. Furthermore, the assay material can be enclosed in a droplet or confined space so that, as the functional nucleic acid probes (FNAPs) act in the confined space, a fluorescence signal is quickly concentrated to detectable signal levels due to the limits of diffusion compared to the total reaction volume. These advantages are also applicable to analyte analysis (with or without of droplets). Additional advantages can include, for RNA targets, no need for reverse transcription, which can be problematic for current methods because non-specific events are more likely to occur during the low-temperature reverse-transcription step and reverse transcriptases are more prone to inhibition than polymerases. Furthermore, nucleic acids are far less expensive to manufacture and are easier to store than proteins (they are more stable than proteins), so there are cost and storage advantages. Another advantage is that the reactions can be isothermal. Thus, cost reduction, increased stability, and workflow simplification are valuable across many applications, particularly for point-of-care devices.

Certain embodiments are directed to a functional nucleic acid probe where the probe is a cleavage-activated catalytic substrate (CACS) comprising a nucleic acid enzyme (NAE) encoded within an enzymatic sequence region (ESR) that is partially bound to an inhibiting sequence region (ISR). In certain aspects the ESR comprises a catalytic core (CC) flanked on both sides by recognition elements/sequences, the recognition elements/sequences anneal or bind to a substrate and functionally orient the CC with respect to the substrate. When the functional nucleic acid probe, which is operating as a substrate or as an binding agent, is cleaved or activated, the inhibiting sequence region is severed or dissociated from the enzymatic sequence region, liberating the nucleic acid enzyme encoded within the enzymatic sequence regions. In certain aspects, the functional nucleic acid probe or a probe composition can comprise at least one functional nucleic acid probe comprising from a first end (3' or 5' end) to a second end (5' or 3' end) one or more of: (a) a first terminus or, optionally, a terminal linker coupled to a quencher or a fluorophore; (b) a first substrate recognition sequence; (c) a catalytic core sequence; (d) a second substrate recognition sequence that is also operable as a landing sequence for a second functional nucleic acid probe; (e) a cleavage site that can be cleaved by the catalytic core sequence of the second functional nucleic acid probe; (f) a second landing sequence for the second functional nucleic acid probe; (g) a linker or spacer region comprising a target binding region/element; (h) a first inhibitory sequence that is complementary to all or some of the first substrate recognition sequence; and (i) a second end or second terminal linker coupled to a fluorophore or a quencher; wherein the first inhibitory sequence or the first inhibitory sequence and the second terminal linker sequesters the first substrate recognition arm when the cleavage site is uncleaved or the binding element is unbound. Upon cleavage the functional nucleic acid probe is activated, that is the nucleic acid enzyme (NAE) is release and is capable of cleaving its substrate or target sequence. The first substrate recognition sequence, the catalytic core, and the second substrate recognition sequence form the nucleic acid enzyme (NAE). In certain aspects the NAE can be a 10-23 DNAzyme, an 8-17 DNAzyme, or a derivative thereof. In a particular aspect the NAE is a G-quadruplex DNAzyme. The linker can comprise an aptamer or other target binding nucleic acid sequence.

Other embodiments are directed to a second functional nucleic acid probe comprising from a first end to a second end: (a) a first terminus or a terminal linker coupled to a quencher or a fluorophore; (b) a first substrate recognition sequence; (c) a catalytic core sequence; (d) a second substrate recognition sequence; and (e) a cleavage site that can be cleaved by the catalytic core sequence of another functional nucleic acid or the second functional nucleic acid probe. The second functional nucleic acid probe can be circular or in plasmid form until cleaved and/or activated. In certain aspects the second functional nucleic probe can be included in a composition having a first functional nucleic acid probe comprising from a first end (3' or 5' end) to a second end (5' or 3' end): (a) a first terminus or, optionally, a terminal linker coupled to a quencher or a fluorophore; (b) a first substrate recognition sequence; (c) a catalytic core sequence; (d) a second substrate recognition sequence that is also operable as a landing sequence for a second functional nucleic acid probe; (e) a cleavage site that can be cleaved by the catalytic core sequence of the second functional nucleic acid probe; (f) a second landing sequence for the second functional nucleic acid probe; (g) a linker or spacer region comprising a target binding region/element; (h) a first inhibitory sequence that is complementary to all or some of the first substrate recognition sequence; and (i) a second end or second terminal linker coupled to a fluorophore or a quencher; wherein the first inhibitory sequence or the first inhibitory sequence and the second terminal linker sequesters the first substrate recognition arm when the cleavage site is uncleaved or the target binding region/element is unbound.

Further aspects are directed to a probe composition that include two or more functional nucleic acid probes. The functional nucleic acid probe composition can have a first functional nucleic acid probe (i) a first terminus or, optionally, a terminal linker coupled to a quencher or a fluorophore; (ii) a first substrate recognition sequence; (iii) a catalytic core sequence; (iv) a second substrate recognition sequence that is also operable as a landing sequence for a second functional nucleic acid probe; (v) a cleavage site that can be cleaved by the catalytic core sequence of the second functional nucleic acid probe; (vi) a second landing sequence for the second functional nucleic acid probe; (vii) a linker or spacer region comprising a target binding region/element; (viii) a first inhibitory sequence that is complementary to all or some of the first substrate recognition sequence; and (ix) a second end or second terminal linker coupled to a fluorophore or a quencher. The composition can further include a second functional nucleic acid probe having (i) a third substrate recognition sequence, (ii) a second catalytic core sequence, (iii) a fourth substrate recognition sequence, and (iv) a second cleavage site that can be cleaved by the catalytic core sequence of the first functional nucleic acid probe. In certain aspects the first functional nucleic probe can be activated by binding a target and, upon activation, binds and cleaves the second functional nucleic probe forming a activated second functional nucleic acid probe. The first cleavage site and the second cleavage site can be the same or different. The first and second recognition sequences can be the same or different than the third and fourth recognition sequences. Landing sequence are complementary to and anneal to a corresponding recognition sequence.

A probe composition of the invention can comprise at least a third functional nucleic acid probe that can be activated by binding a target, and, upon activation, binds and cleaves a fourth functional nucleic acid probe that, upon activation, binds and cleaves a functional nucleic acid as described above for a first functional nucleic acid probe.

Methods for analyzing analytes can comprise: (a) providing a plurality of partitions comprising at least one target, a plurality of allosteric functional nucleic acid probes, a plurality of oligonucleotide probe substrates, and constituents required for analyte binding, substrate binding, and substrate catalysis; (b) incubating the partitions with the probes, probe substrates, and constituents wherein at least one probe binds the target; (c) binding of the target activates a nucleic acid enzyme within the probe that continuously catalyzes a reaction throughout the incubation, whereby the product of the reaction releases a detectable label; and (d) producing an accumulation of detectable label within the partition; and (e) detecting the detectable label and associating it with the presence of the target. The partitions can comprise droplets in an immiscible fluid. In certain aspects the droplets are arranged in a static two-dimensional array monolayer for incubation and detection. The immiscible fluid can be a fluorocarbon comprising a fluorosurfactant. In certain aspects the droplet partitions are generated using Laplace pressure gradients, shear stress, or other methods known to form droplets. Detection can be performed using a camera having a plurality of emission filters and magnifications. In certain aspects detection can be performed using a plurality of LEDs combined with a plurality of excitation filters. The nucleic acid enzyme can be an endonuclease. Oligonucleotide probe substrates can be labeled with a fluorophore and a quencher wherein the fluorophore is separated from the quencher after endonucleatic cleavage. The oligonucleotide probe substrates can be functional nucleic acids. In certain aspects oligonucleotide probe substrates are stem-loop structures. The individual oligonucleotide probe substrates can have different melt temperatures. In certain aspects, the allosteric functional nucleic acid probes can be or include DNA, RNA, PNA, L-DNA, L-RNA, or combinations thereof. In certain aspects the functional nucleic acid probe comprises an aptazyme or allosteric aptazyme. The nucleic acid enzyme can be a 10-23 DNAzyme or derivative thereof; an 8-17 DNAzyme or derivative thereof; a G-quadruplex DNAzyme or derivative thereof; or a similar enzymatic endonuclease. The partitions can include cell viability reagents. The cell viability reagents can be resazurin-based or tetrazolium-based cell viability reagents. The cell viability reagents can further include protease markers. In certain aspects, all or a fraction of the partitions can include an environmental stressor(s). In certain aspects the environmental stressors include drugs used to treat the target cell. Drugs can include antimicrobials, chemotherapies, and the like. The target can be on, secreted from, or released from a target cell. In a further aspect, the oligonucleotide probe substrate is a cleavage-activated catalytic substrate comprising a nucleic acid enzyme encoded within an enzymatic sequence region that is partially bound to an inhibiting sequence region and when the substrate is cleaved, the inhibiting sequence region is severed from the enzymatic sequence region, liberating the nucleic acid enzyme encoded within the enzymatic sequence regions. The method can include an exponential deoxyribozyme ribonuclease cleavage cascade (DRCC) that is initiated by the liberated nucleic acid enzyme which then bind to a loop region of another functional nucleic acid probe whose sequence is identical to the functional nucleic acid probe which cleaved the parent stem-loop of the liberated nucleic acid enzyme; catalyze the cleavage of the functional nucleic acid probe, bypassing the allosteric sequence region by severing the inhibiting sequence region from the enzymatic sequence region, which is irreversibly activated and able to the cleave a loop-stem of another cleavage-activated catalytic substrate probe identical to the probe that activated the functional nucleic acid probe. The number of cleavage events in the reaction can grow exponentially. The functional nucleic acid probes can be stem-loops comprising a fluorophore and a quencher.

Certain embodiments are directed to methods for analyzing target cells. The methods can include one or more of the following steps: (a) providing a plurality of partitions comprising at least one target cell, a plurality of allosteric functional nucleic acid probes, a plurality of oligonucleotide probe substrates, and constituents required for target binding, substrate binding, and substrate catalysis; (b) incubating the partitions with the probes, probe substrates, and constituents wherein, in at least one probe, a analyte-binding allosteric sequence region in the probe binds to a target analyte on the surface of the target cell; (c) denaturing an inhibiting sequence region in the probe from an enzymatic sequence region in the probe wherein the enzymatic sequence region encodes a nucleic acid enzyme; (d) permitting the nucleic acid enzyme to bind specifically to an oligonucleotide substrate wherein the substrate comprises a detectable label; (e) cleaving the oligonucleotide substrate, splitting it into two oligonucleotides that denature from the probe and each other, resulting in the release of the detectable label; (f) permitting the nucleic acid enzyme to bind and cleave another oligonucleotide probe substrate, and the process of binding, cleaving, and denaturing occurs continuously throughout the incubation, resulting in an accumulation of detectable label within the partition; and (g) detecting the detectable label and associating it with the target cell.

Further embodiments are directed to methods for analyzing target cells. The methods can include one or more of the following steps: (a) providing a sample comprising at least one target cell, a plurality of allosteric functional nucleic acid probes, a plurality of oligonucleotide probe substrates, and constituents required for target binding, substrate binding, and substrate catalysis; (b) incubating the sample with the probes, probe substrates, and constituents wherein, in at least one probe, a analyte-binding allosteric sequence region in the probe binds to a target analyte on the surface of the target cell; (c) denaturing an inhibiting sequence region in the probe from an enzymatic sequence region in the probe wherein the enzymatic sequence region encodes a nucleic acid enzyme; (d) permitting the nucleic acid enzyme to bind specifically to an oligonucleotide substrate wherein the substrate comprises a detectable label; (e) cleaving the oligonucleotide substrate, splitting it into two oligonucleotides that denature from the probe and each other, resulting in the release of the detectable label; (f) permitting the nucleic acid enzyme to bind and cleave another oligonucleotide probe substrate, and the process of binding, cleaving, and denaturing occurs continuously throughout the incubation, resulting in an accumulation of detectable label within the sample; and (g) detecting the detectable label and associating it with the target cell.

Still further embodiments are directed to methods for analyzing target nucleic acids can include one or more of the following steps: (a) providing a plurality of partitions comprising at least one target nucleic acid sequence, a plurality of allosteric functional nucleic acid probes, a plurality of oligonucleotide probe substrates, and constituents required for target binding, substrate binding, and substrate catalysis; (b) incubating the partitions with the probes, probe substrates, and constituents wherein, in at least one probe, an allosteric sequence region in the probe is complementary to a target nucleic acid sequence and binds to the target sequence; (c) denaturing an inhibiting sequence region in the probe from an enzymatic sequence region in the probe wherein the enzymatic sequence region encodes a nucleic acid enzyme; (d) permitting the nucleic acid enzyme to bind specifically to an oligonucleotide substrate wherein the substrate comprises a detectable label; (e) cleaving the oligonucleotide substrate, splitting it into two oligonucleotides that denature from the probe and each other, resulting in the release of the detectable label; (f) permitting the nucleic acid enzyme to bind and cleave another oligonucleotide probe substrate, and the process of binding, cleaving, and denaturing occurs continuously throughout the incubation, resulting in an accumulation of detectable label within the partition; and (g) detecting the detectable label and associating it with the target nucleic acid sequence. In certain aspects a functional nucleic acid probe includes allosteric functional nucleic acid probes and oligonucleotide probe substrates The target nucleic acid can be secreted from a cell.

Certain embodiments are directed to methods for analyzing target nucleic acids can include one or more of the following steps: (a) providing a sample comprising at least one target nucleic acid sequence, a plurality of allosteric functional nucleic acid probes, a plurality of oligonucleotide probe substrates, and constituents required for target binding, substrate binding, and substrate catalysis; (b) incubating the sample with the probes, probe substrates, and constituents wherein, in at least one probe, an allosteric sequence region in the probe is complementary to a target nucleic acid sequence and binds to the target sequence; (c) denaturing an inhibiting sequence region in the probe from an enzymatic sequence region in the probe wherein the enzymatic sequence region encodes a nucleic acid enzyme; (d) permitting the nucleic acid enzyme to bind specifically to an oligonucleotide substrate wherein the substrate comprises a detectable label; (e) cleaving the oligonucleotide substrate, splitting it into two oligonucleotides that denature from the probe and each other, resulting in the release of the detectable label; (f) permitting the nucleic acid enzyme to bind and cleave another oligonucleotide probe substrate, and the process of binding, cleaving, and denaturing occurs continuously throughout the incubation, resulting in an accumulation of detectable label within the sample; and (g) detecting the detectable label and associating it with the target nucleic acid sequence. In certain aspects a functional nucleic acid probe includes allosteric functional nucleic acid probes and oligonucleotide probe substrates The target nucleic acid can be secreted from a cell.

In still other embodiments of the invention are directed to methods for analyzing analytes including one or more steps of: (a) providing a plurality of partitions comprising at least one analyte, a plurality of allosteric functional nucleic acid probes, a plurality of allosteric analyte-binding oligonucleotides, a plurality of oligonucleotide probe substrates, and constituents required for analyte binding, substrate binding, and substrate catalysis; (b) incubating the partitions with the probes, analyte-binding oligonucleotides, probe substrates, and constituents wherein a analyte-binding allosteric sequence region in at least one allosteric analyte-binding oligonucleotides binds to a target analyte; (c) exposing a sequence region in the allosteric analyte-binding oligonucleotide that is complementary to and binds to the allosteric sequence region of at least one nucleic acid probe; (d) initiating a continuous catalytic reaction that produces a detectable label, resulting in an accumulation of detectable label within the partition; and (e) detecting the detectable label and associating it with the target analyte.

Certain embodiments are directed to methods for analyzing target cells within a test sample, the methods including one or more steps of: (a) providing a test sample comprising at least one target cell; (b) combining the test sample with a plurality of functional nucleic acid probes comprising a nucleic acid enzyme and a target recognition region; (c) incubating the combination until the target recognition region in at least one probe binds to a target cell; (d) separating the probe-cell complex from any unbound probes; (e) combining the probe-cell complex with a plurality of labeled oligonucleotide probe substrates and constituents required for substrate binding and catalysis; (f) partitioning the combination; (g) incubating the partition wherein the nucleic acid enzyme in the bound probes continuously catalyzes the cleavage of its oligonucleotide substrate wherein the product of the catalysis releases a detectable label; (h) resulting in an accumulation of detectable label within the partition; and (i) detecting the detectable label and associating it with the target cell.

One or more method or reaction of the current invention can include probes at a concentration between 1, 10, 100 pM to 0.1, 1, 10 µM. In certain aspect the probes can be present in a concentration ranges of between 1, 10, 50 nM to 75, 100, 150, 200 nM. The probes can be assayed using a pH range 6 to 9. In certain aspects the pH of an assay or composition is between pH 7 and 7.5. The pH can be adjusted to optimize the enzymatic activity of a probe, with higher pH assisting with deprotonating the RNA 2' hydroxyl. Reactions can also include additional constituents, such as $MgCl_2$. In certain aspects the $MgCl_2$ concentration ranges from 1 mM, 2, mM, 10 mM, 25 mM, 50 mM, 100 mM, including all ranges and values there between. NaCl can also be included in a reaction mixture. NaCl concentration can vary between 10, 25, 50 mM to 75, 100, 150 mM, including all values and ranges there between.

The term "target" as used herein indicates an analyte of interest that is to be detected. The term "analyte" refers to a substance, compound, moiety, or component whose presence or absence in a sample is to be detected. Analytes include but are not limited to molecules and biomolecules. The term "biomolecule" as used herein indicates a substance, compound or component associated with a biological environment including but not limited to sugars, amino acids, peptides, proteins, and oligonucleotides/nucleic acids.

The terms "detect" or "detection" as used herein indicates the determination of the existence, presence or fact of a specific target in a limited portion of space, including but not limited to a sample, a reaction mixture, or other limited portion of space identifiable to a skilled person upon a reading of the present disclosure. In certain non-limiting aspects the space is a confined space such as a droplet as described herein. The detection can be quantitative or qualitative. A detection is "quantitative" when it refers to, relates to, or involves the measurement of quantity or amount of the target or signal (also referred as quantitation), which includes but is not limited to any analysis designed to determine the amounts or proportions of the target or signal. Detection is "qualitative" when it refers to, relates to, or involves identification of a quality or kind of the target or signal in terms of relative abundance to another target or signal, which is not quantified.

The term "binding agent" or "binding element" as used herein indicates a molecule or portion of a molecule that can specifically bind to a target, e.g., through the specific binding of one or more of molecule binding sites. Binding agent/element herein described can include molecules of various chemical natures such as polynucleotides (e.g. DNA or RNA), including aptamers, as well as other molecules capable of specific binding in the context of the compositions described herein which are identifiable by a skilled person upon reading of the present disclosure. In some embodiments, an functional nucleic acid or functional nucleic acid segment can be used to specifically bind or capture an analyte for detection.

Aptamers are functional synthetic nucleic acids optimized for high-affinity binding to targets (e.g., nucleic acids, proteins, and chemical compounds). Unlike naturally occurring nucleic acids, which are optimized with respect to transfer of genetic information, aptamers are selected on the basis of their ability to specifically bind their analyte. Systematic Evolution of Ligands by Exponential Enrichment (SELEX) is a process of selecting aptamers directed to a chosen ligand. See U.S. Pat. Nos. 5,475,096, 5,595,877, 5,660,985, and 6,180,348. The SELEX process selects aptamers by screening random sequence libraries, retaining sequences that bind the chosen target molecule, and repeating the cycle with increasing levels of binding stringency. The selected aptamer is capable of binding a chosen target but not other molecules.

Allosteric nucleic acids have a binding site that, in the presence of a sufficient amount of analyte, alters the conformation of the nucleic acid to its active conformation or release of an associated inhibition.

The term "link" or "coupled" and forms thereof, are intended to mean either an indirect or direct connection. Thus, if a first component links to a second component, that connection may be through a direct connection or through an indirect connection via other components and connections.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the transitional phrases "consists of" and "consisting of" exclude any element, step, or component not specified. For example, "consists of" or "consisting of" used in a claim would limit the claim to the components, materials, or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between the open ended "comprising" and closed "consisting of".

Certain terms are used throughout the following description and claims to refer to particular system components and method steps. As one skilled in the art will appreciate, different products may refer to a component by different names. This document does not intend to distinguish between components that differ in name but not function.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

For a more complete understanding of the present disclosure, and the advantages thereof, reference is now made to the following descriptions taken in conjunction with the accompanying drawings, in which:

FIG. 11 illustrates a linear depiction of a probe P sequence.

FIG. 12 illustrates array notation for nucleic acid strands and domains.

FIG. 13 illustrates target recognition integrated into a Ping-Pong probe. Region 5 creates a toe-hold for the target to displace ISR sequence domains 6' and 1', allosterically activating the probe.

DETAILED DESCRIPTION

Figure 1:
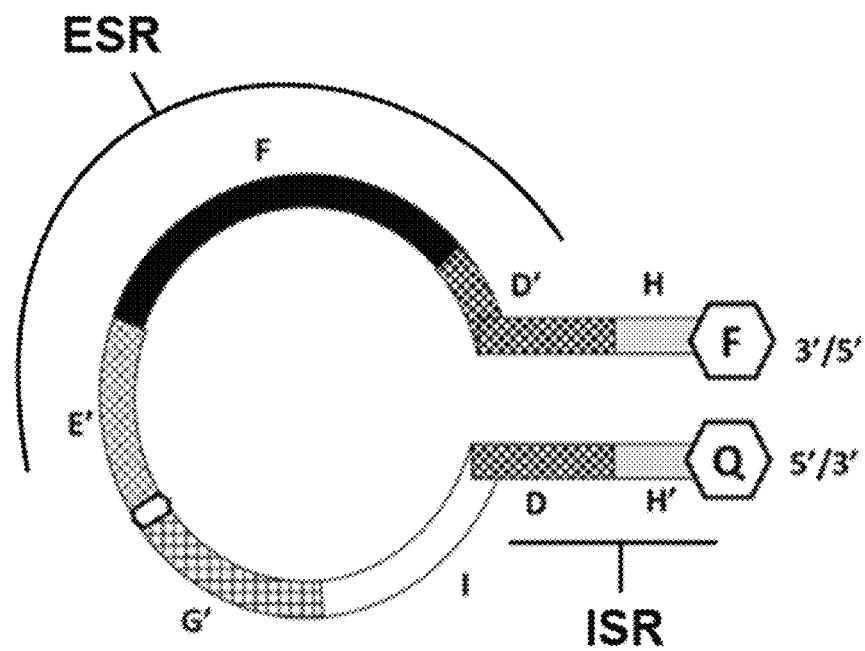
FIG. 1 illustrates a general component of a Ping Pong Probe composition.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to imply that the scope of the disclosure, including the claims, is limited to that embodiment.

The invention generally relates to compositions and methods for detecting and/or characterizing analytes or cells. The following sections discuss general considerations and design for functional nucleic acid probes, test samples, analysis reagents, multiplexing, compartmentalization, signal detection, and cell viability.

Embodiments of the invention offer several advantages over existing methods. In certain aspects of the current invention, cellular or bacterial surface biomarkers are used for identification, thus cell lysis is not required. Another advantage is that surface biomarkers are available for all targets, enabling the technique to be equally effective across cell types and pathogen species. In addition, there is natural amplification for a target cell compared to a single genome target per cell because there are a plurality of surface biomarkers present, some in the tens of thousands. Furthermore, the assay material can be, but need not be, enclosed in a droplet so that, as the functional nucleic acid probes (FNAPs) act in a confined space, a fluorescence signal is quickly concentrated to detectable signal levels due to the limits of diffusion compared to the total reaction volume. One aspect of the invention is that a single binding event produces a cascade resulting in signal generating events since each bound FNAP continuously cleaves substrate. Combining multiple targets with a limited diffusion for an ongoing reaction produces signal very quickly. For those cells that are not populated significantly by any single biomarker, the same enzymatic sequence region (ESR) can encode multiple allosteric sequence regions (ASRs) for a single cell. Finally, multiple ESRs can be attached to a single ASR, by simply placing them in the same nucleic acid strand. Therefore, the invention offers significant flexibility in ensuring that the reaction occurs more quickly than many NATs.

Other aspect includes isothermal or substantially isothermal amplification, where the substrate cleavage reaction occurs at a single temperature. This isothermal aspect of the invention obviates the need for thermal cycling equipment, which can add cost and workflow complexity. Also, by avoiding high temperatures, the invention avoids significant issues that can arise with fluid evaporation and/or bubbles that can disrupt the integrity of the reaction and/or the fluorescent readout.

FNAPs are inexpensive compared to protein enzymes and because of their simple structure, they can be easily solubilized and are less likely to be inhibited. Because FNAP enzymatic activity is allosterically activated, in certain aspects, when the ASR binds to its target, this method obviates the need for a wash step prior to portioning the sample in order to remove unbound probes, enabling FNAP incubation to occur within the droplets rather than in bulk solution where any signal generated by bound probes would be lost to diffusion. Therefore, by maximizing signal generation during FNAP incubation, allosteric activation of FNAP enzymatic activity accelerates cell identification. Similarly, if cell viability is included in the analysis, obviating the need for a bulk incubation prior to compartmentalization also minimizes the time required to generate a measurable viability signal within a droplet. Finally, this method does not require the cells be fixed or expensive optical equipment.

Target cells, analytes, or samples containing target cells or analytes can be mixed or re-suspended with functional nucleic acid probes (FNAPs), along with the FNAP's nucleic-acid substrate, and, in certain embodiments, the suspension is compartmentalized into droplets. The nucleic-acid substrate contains a fluor or other detectable label and quencher pair that remains almost entirely quenched when the substrate is in a loop-stem hairpin state. Each FNAP comprises an allosteric sequence region (ASR) and an enzymatic sequence region (ESR) whereby the ASR activates the ESR when it binds to its target. Within a sampled or droplet containing a target cell, the FNAPs with ESRs activated by a bound ASR will cleave their specific substrate causing the sample or droplet they are in to fluoresce as fluor-quencher pairs are separated. The fluorescence dye can encode for a target cell or an analyte. One or more fluorescence dyes can be used to encode a cell or analyte, and because, in certain embodiments, single cell types are isolated within a droplet, two or more dye combinations can be used to identify target cells using binary encoding, thus expanding the multiplex capability beyond the total number of dyes used (digital representation).

As a general scheme, a test sample comprising at least one target cell or analyte is combined with analysis reagents. The analysis reagents can include functional nucleic acid probes (FNAPs). In certain aspects the target cell and reagents can be, but need not be, partitioned into microdroplets such that a statistically significant number of droplets contain no more than one target cell. In certain aspects, the partitions or sample are incubated and probes selectively bind to the target cell activating a nucleic acid enzyme region within the probe. The activated nucleic acid enzyme region catalyzes a cell-specific signal-generating reaction which is interpreted by an optical transducer. Further details on the processes of the invention are provided below.

A. Functional Nucleic Acid Probes

Functional nucleic acids (FNAs) include nucleic acids whose functions extend beyond the conventional genetic roles of nucleic acids. Functional nucleic acids of the invention can comprise one or more binding regions (e.g., aptamers), nucleic acid enzymes (NAEs), and/or aptazymes. Functional nucleic acid probes (FNAPs) are FNAs used to produce a detectable signal (e.g., fluorescence) when a target analyte is present in a sample.

Certain embodiments of the invention use allosteric functional nucleic acid probe (AFNAP) that comprise an allosteric sequence region (ASR) that recognizes and binds to a target (e.g., protein, nucleic acid, etc.), the binding altering the confirmation of the probe releasing the inhibition of an inhibiting sequence region (ISR) (e.g., denaturing a hair-pin or other structure). In certain aspects, the ISR restricts access to or inhibits the function of a nucleic acid enzyme (NAE) encoded in the enzymatic sequence region (ESR) of the probe. Thus, the ASR activates the NAE upon binding to its target, the NAE is released/uninhibited and is free to catalyze cleavage of its nucleic acid substrate. Upon cleavage, the nucleic acid substrate is released from an inactive configuration (e.g., denaturing a hair-pin or other structure) freeing up a second enzyme to catalyze the cleavage of another substrate. This process is continuously repeated as long as the enzymatic sequence regions remain free or uninhibited (i.e., activated). Therefore, a single activated probe catalyzes the cleavage of many oligonucleotide substrates/substrates and generates additional NAEs over a reaction period.

The oligonucleotide substrate can be a hairpin-substrate with a fluor or other detectable label associated with a quencher in close proximity by virtue of a paired double-helix in the hairpin stem, the fluor or detectable label being in a quenched configuration. Upon cleavage, there is a resulting increase in entropy that increases the free energy required to maintain the nucleic acid structure (e.g., double helix) and it denatures or dissociates, separating the fluor and quencher and generating an unquenched fluor or active flour.

In certain aspects, the hairpin-stem duplex can be designed to denature at different temperatures which can be used to encode additional target information because multiple probes can be used for a single fluorescence channel. In this embodiment, a diminished change in fluorescence intensity over temperature indicates that the target was present for the probe that cleaves the hairpin-loop associated with the hairpin-stem that denatures at that temperature. In other aspects, the oligonucleotide substrate can be a linear oligonucleotide.

In certain embodiments the binding of a probe as described herein results in a deoxyribozyme ribonuclease cleavage cascade (DRCC). Aspect of the DRCC are provided.

DRCC Functional Blocks.

DRCC is a technique for target-initiated exponential signal amplification that offers cost, robustness, and sample workflow advantages over protein-mediated reactions. Conceptually, the nucleic-acid-only DRCC reaction can be broken down into two functional blocks: (1) a target-initiated "trigger" and (2) exponential signal amplification. In some embodiments, these two functions are integrated onto the same probes. In other embodiments the functions can be incorporated into separate probes or components. Separating the functions can greatly simplify probe design verification and optimization.

Exponential Signal Amplification Using Ping Pong Probes.

In DRCC, exponential signal amplification is accomplished through a complementary pair of probe species or components (e.g., probe S and probe P, see FIG. 3) whereby the enzymatic activity of a probe from a first probe species or component is activated by the enzymatic activity of a probe from a second probe species or component (described below). Once activated, the activated probe from the first probe species or component can, in turn, activate a probe from the second probe species or component, which can, in turn, activate another probe from the first probe species or component, and so on and so forth. Activation "ping-pongs" back and forth between probe species (for example see FIG. 3). Ping Pong probes comprise the core of the DRCC reaction, much as primers are the core of the PCR reaction Like primers, Ping Pong probes are always paired. However, unlike PCR primers, Ping Pong probes do not always interact with the target.

Probe components involved in DRCC encode an Enzymatic Sequence Region (ESR) that is activated by the other probe species or components. In at least one of the probe species, the ESR is in a deactivated state by association with an Inhibiting Sequence Region (ISR) which blocks access to the DNAzyme encoded by the ESR, as shown schematically in FIG. 1 and FIG. 2 (Probe S).

FIG. 1 depicts a generalized Ping Pong probe component. The Enzymatic Sequence Region (ESR) include a first recognition arm segment (E') couple to an enzymatic core segment (F) which is further coupled to a second recognition arm (D') forming an ESR (E'FD'). The second recognition arm (D') can be coupled to an optional terminal linker (H) that can be further coupled to quencher or detectable label (e.g., fluor). The probe is initially configured with ESR being associated with an Inhibiting Sequence Region (ISR). The ISR can include a first inhibitory segment (D) that is complementary to at least a portion of the second recognition arm (D') and a second inhibitory segment (H') that is complementary to all or part of the terminal linker (H). The ISR forms a complement (DH') to all or part of the second recognition arm/terminal linker portion (D'H) of the probe. The ISR is designed to complement and anneal to a portion of the ESR and block or inactivate the function of the second recognition arm of the ESR, with the ESR and ISR annealed the probe is enzymatically inactive. A cleavage site is positioned between the ESR and ISR portion of the probe. The cleavage site includes a first and second enzyme binding or landing sequence (E'G') flanking a cleavage site that is a substrate for enzymatic core segment (F), i.e., a catalytic core (CC)). In certain aspects the first binding arm or landing site (E) is equivalent to the first recognition arm (E') and provides for binding or landing of an enzyme having a segment functionally equivalent to the second recognition arm (D'). The second binding arm or landing site (G') provides for binding of an enzyme having recognition arm that is equivalent to first recognition arm (E'). When an enzyme comprising the first and second recognition arms or landing sites (E'FD') anneal to the catalytic cleavage site (E'G') cleavage can occur resulting in the uncoupling of the ESR and the ISR, which leads to activation of the cleaved probe. That is, the ESR is activated upon cleaving the probe hairpin loop by the entropically favored release of the ISR. A spacer (I) can be used to provide flexibility or spacing in the probe to allow various aspects of the probe or its activators to properly interact.

In the embodiments described thus far, the NAEs encoded in the ESR are nucleic acid cleaving NAEs. Examples of NAEs include the 10-23 and 8-17 DNAzymes and derivatives thereof, including the 17E DNAzyme which is a derivation of the 8-17 DNAzyme, and L-RNA cleaving 10-23 and 8-17 DNAzymes and L-DNAzymes. Other embodiments can comprise a G-quadruplex DNAzyme which does not cleave a nucleic acid substrate. Instead it recruits hemin as a cofactor with peroxidase activity.

Figure 2:
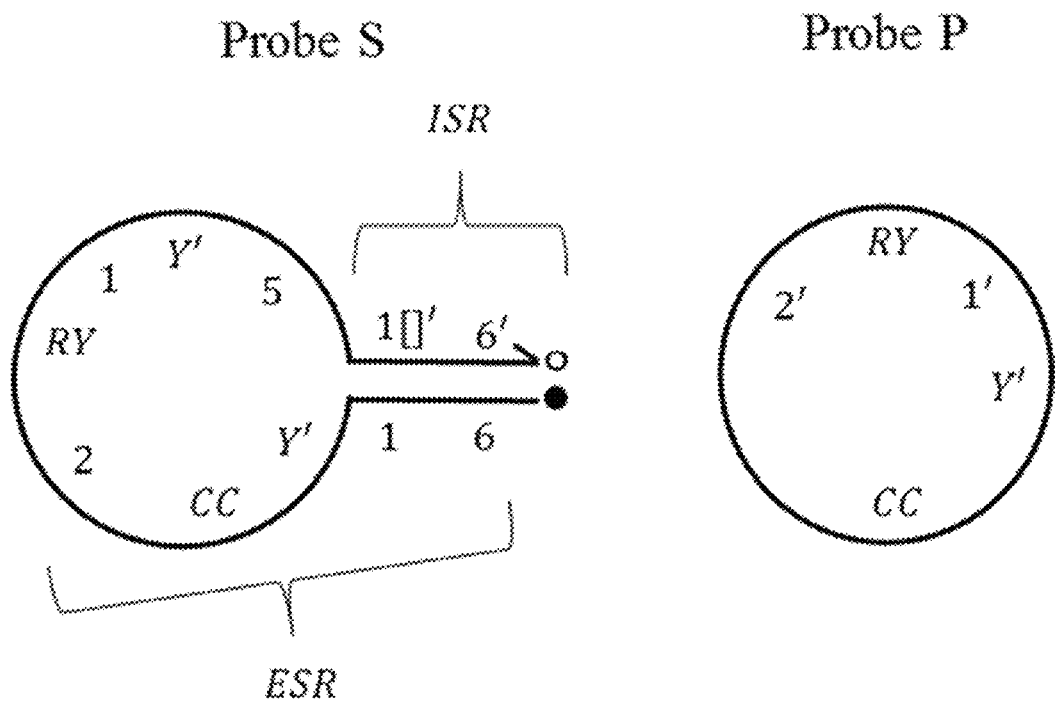
FIG. 2 illustrates Ping Pong Probes, S and P, encoding 10-23 DNAzyme (2/CC/Y'/1), for example.

DRCC using 10-23 Deoxyribozyme (DNAzyme). In DRCC, signal amplification can be carried out by a pair of complementing Ping Pong probes, depicted in FIG. 2 (Probe S and Probe P). The enzymatic sequence regions of the Ping Pong probes used here each encode an NAE, e.g., a 10-23 DNAzymes (1/CC/2 and 1'/CC/2'). However, the same design principles can be used for any deoxyribozyme with an RNA-cleaving or DNA-cleaving moiety, including but not limited to the 8-17 DNAzyme, and all derivations thereof (e.g., 17E DNAzyme), with the obvious caveat that the catalytic core sequence (CC) will be altered. When the ESRs used in DRCC comprise 10-23 DNAzymes, the ISR is entropically driven away from the ESR when the purine-pyrimidine junction (RY) in the hairpin loop is cleaved by the ESR of the other probe species or component (see for example FIG. 3). While the hairpin probe design (S) depicted in FIG. 2 can be used for both Ping Pong probes, it is advantageous to pair a hairpin probe (S) with a complementary probe or circular probe (P) as shown in FIG. 2. This simplifies the design because it obviates the need to design and optimize a second ISR. Most importantly, it also minimizes potential for non-specific probe interactions between probe species.

Figure 3:
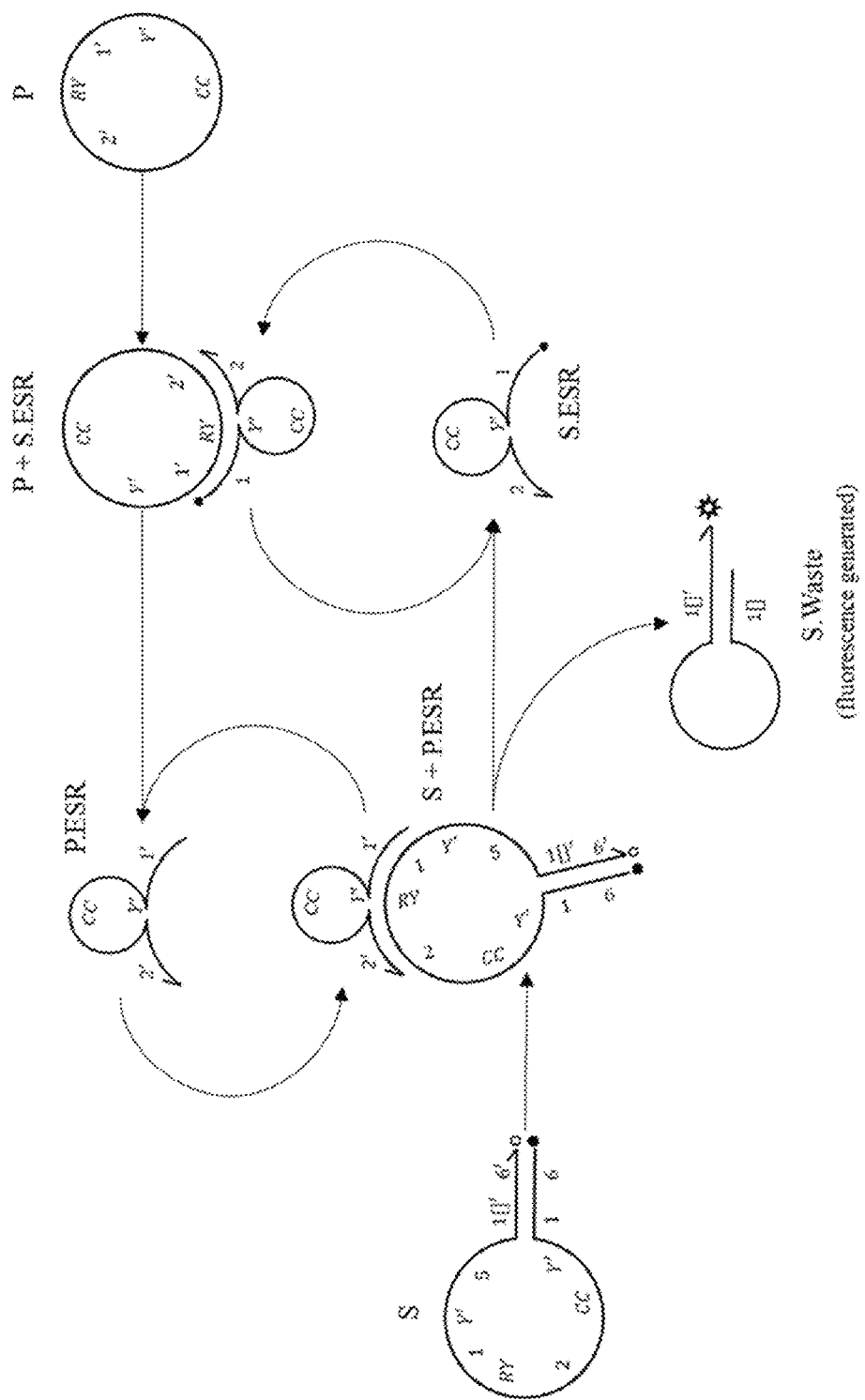
FIG. 3 illustrates DRCC using 10-23 DNAzyme encoded in probe ESRs (P.ESR and S.ESR).

In probe P, rather than using a hairpin stem to inhibit the probe P ESR, it is deactivated by ligation of the ESR's 5' and 3' ends (sequence domains 1' and 2', respectively) to form a circular molecule. When confined to a circular DNA strand, P's substrate arms, 1' and 2', cannot bind to the substrate on the complementary probe S, because they are not free to lay across the binding or landing site as a paired duplex. Cleavage of the cleavage site (RY) linearizes probe P providing an active 1 '/CC/2' ESR. Signal generation is achieved by cleavage of probe S at RY and separation of the fluor-quencher pair upon cleavage of S by the ESR of probe P (FIG. 3).

Probe Design.

Figure 4:
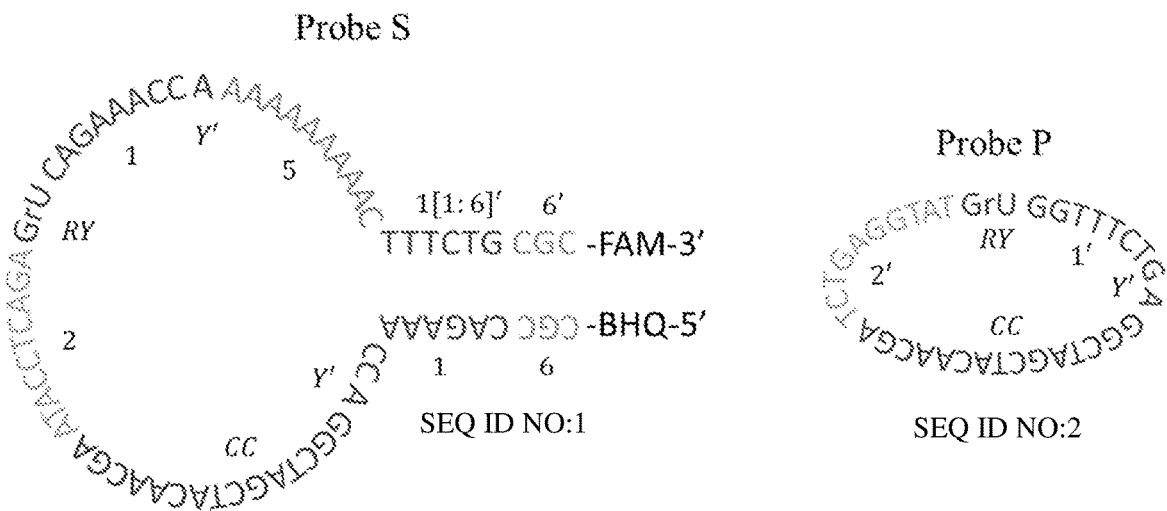
FIG. 4 illustrates a sequence design for a probe S and P.

FIG. 4 displays an example of a complete sequence design for probes S (SEQ ID NO:1) and P (SEQ ID NO:2) using the following reaction conditions: 150 mM NaCl, 25 mM $MgCl_2$, and 37° C. Amplification can be designed to occur at any temperature but 37° C. is frequently used because many applications occur at physiological conditions. The ESR in both probes, S (S.ESR) and P (P.ESR), encodes a 10-23 DNAzyme, represented by sequence domains: 1/Y/CC/2 (5' to 3') as S.ESR and 1'/'CC/2' as P.ESR.

Probe Thermodynamics.

Figure 5:
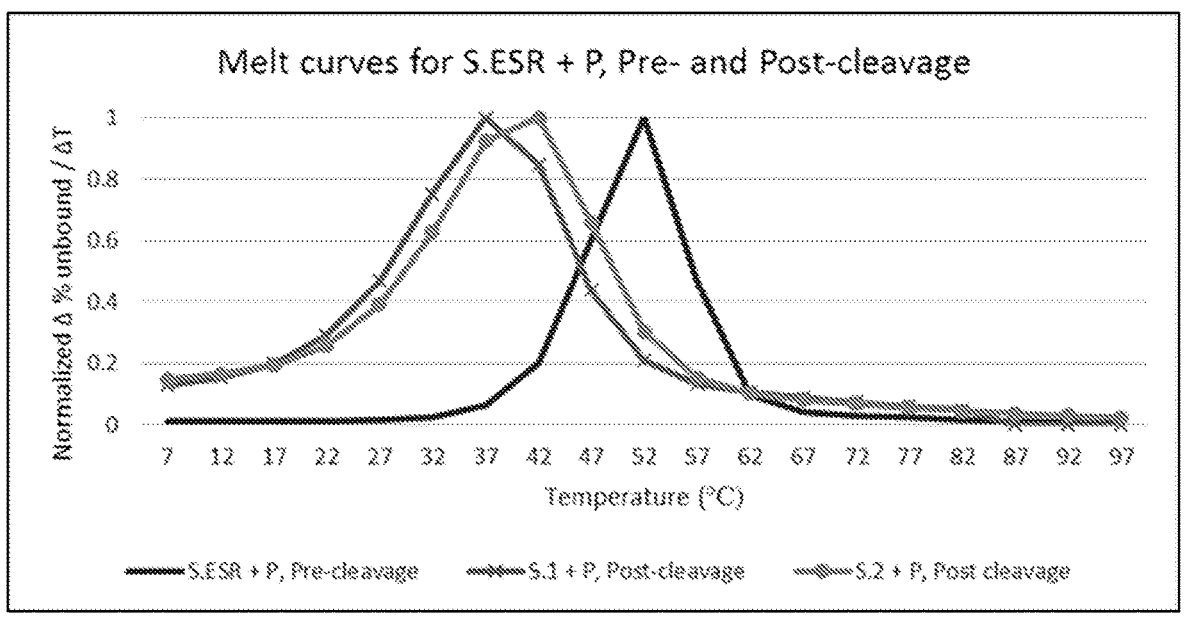
FIG. 5 illustrates a normalized S.ESR melt curves pre- and post-cleavage.
Figure 6:
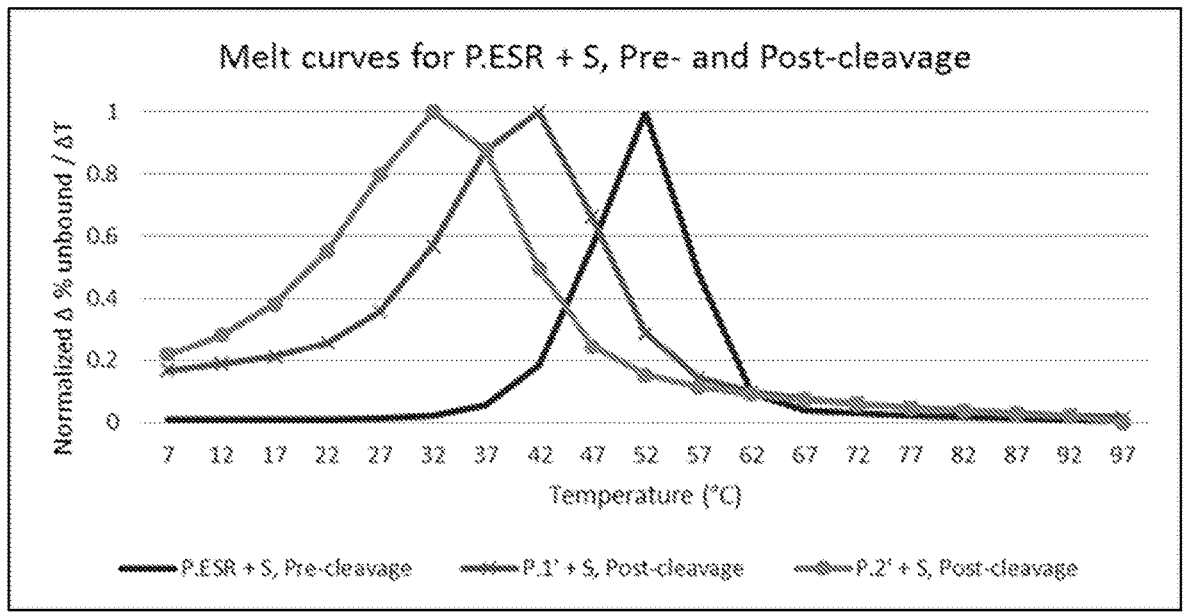
FIG. 6 illustrates a normalized P.ESR melt curves pre- and post-cleavage.

ESR pre- and post-cleavage (S.ESR+P and P.ESR+S). It is critical to design 1, 2, 1', and 2' so that S.ESR and P.ESR strongly bind to the probe substrate landing site on P (1' and 2') and S (1 and 2), respectively, but can also denature efficiently post cleavage, allowing a single ESR to continuously and efficiently cleave the complementary probe species. As a general rule, setting the melt temperature of the individual substrate arms at or near the reaction temperature (37° C.) will produce strong ESR binding pre-cleavage (S.ESR+P, P.ESR+S) and also allow the ESR to efficiently denature post-cleavage (see FIG. 5 and FIG. 6).

ISR Pre- and Post-Cleavage (S.ISR).

Figure 7:
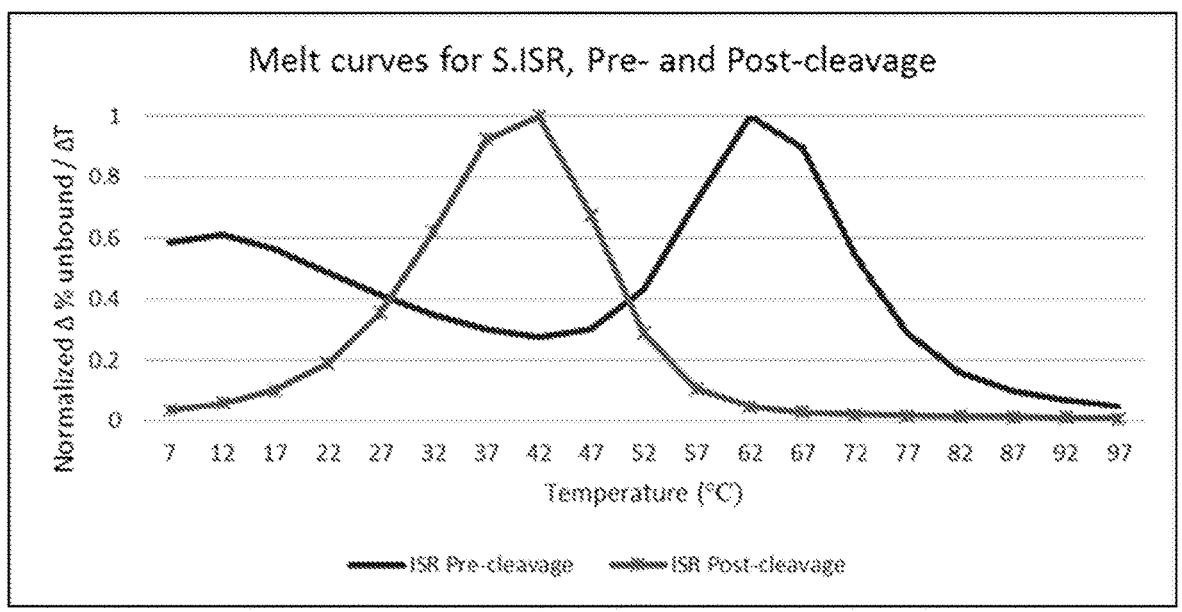
FIG. 7 illustrates melt curves for S.ISR pre-cleavage (hairpin stem) and post-cleavage (duplex).

To keep S.ESR from activating non-specifically throughout the reaction, S.ISR is designed to remain strongly bound to recognition arm 1. However, much like the ESR pre- and post-cleavage, it is also important that S.ISR denatures efficiently from S.ESR post-cleavage. This is best accomplished by setting the post-cleavage S.ISR duplex melt temperature to the reaction temperature (FIG. 7).

S.Waste Hairpin.

Figures 8, 9:
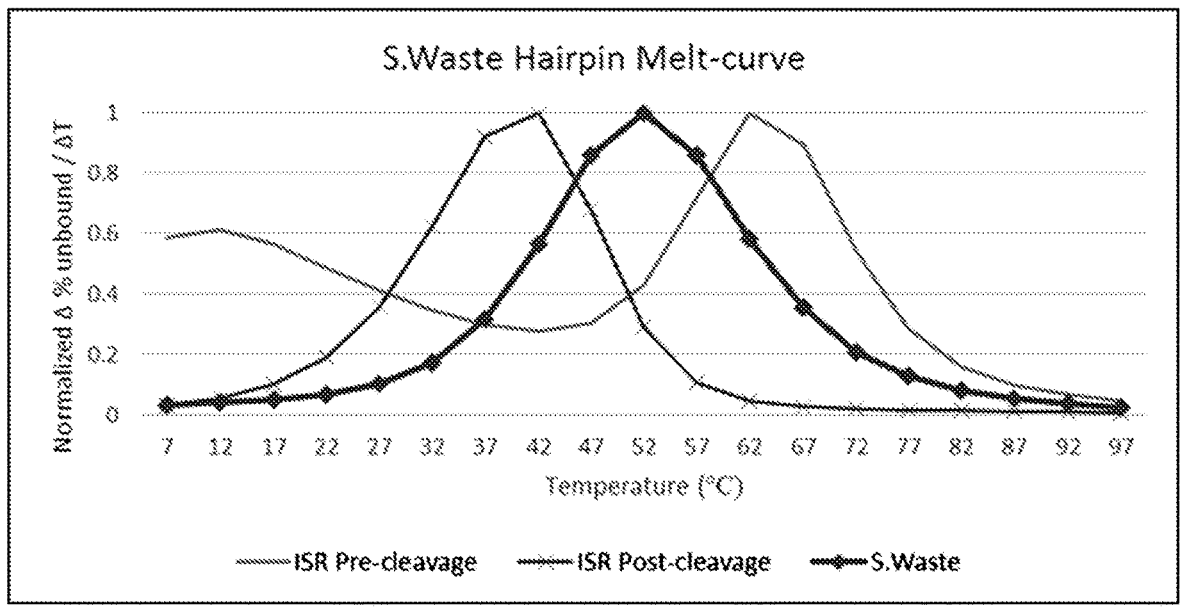
FIG. 8 illustrates S.Waste Tm sandwiched between the ISR pre- and post-cleavage Tms.
FIG. 9 illustrates a linear depiction (5' to 3') of probe S sequence domains.
Figure 10:
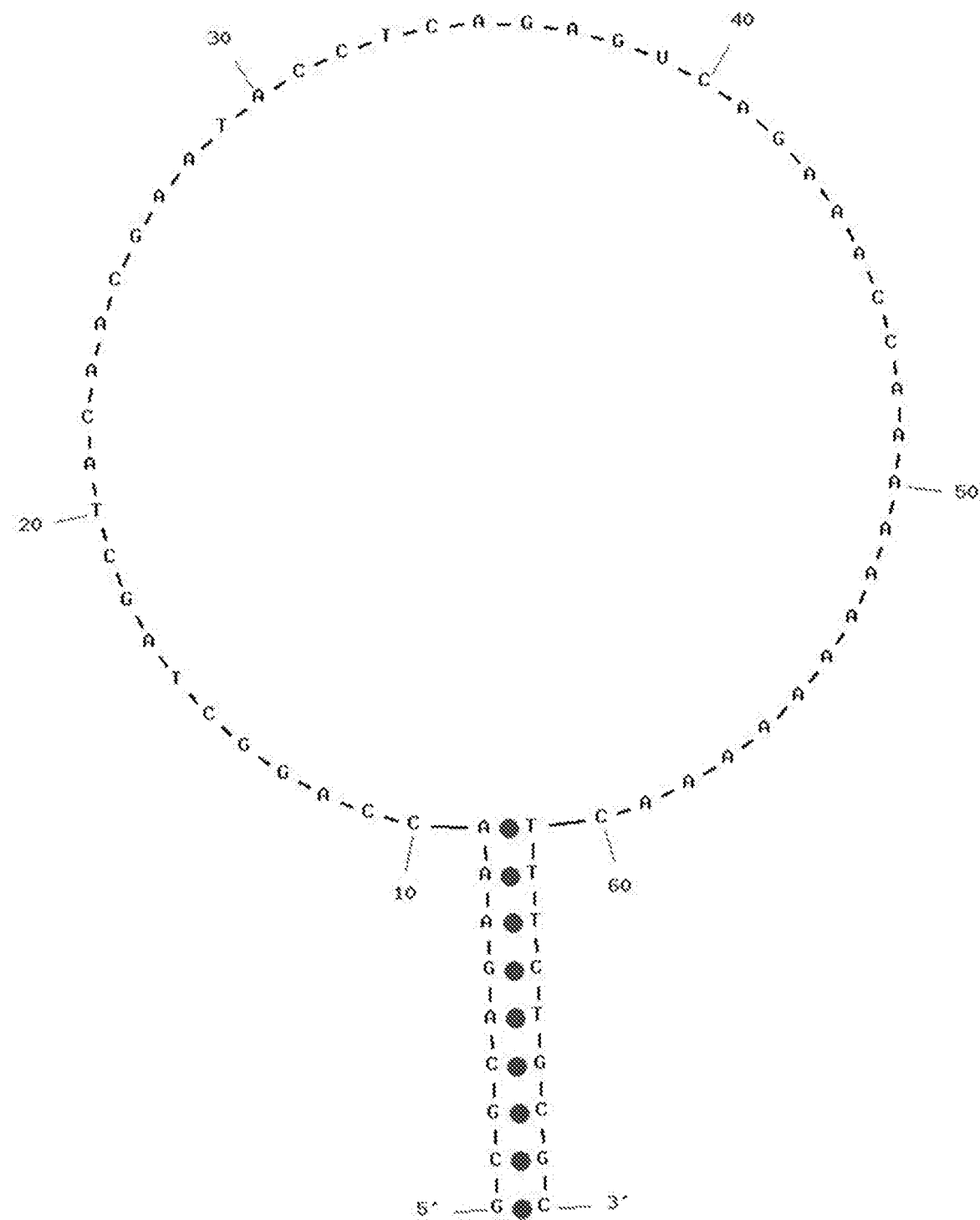
FIG. 10 illustrates an M-fold simulation of the probe S design in FIG. 9.

In certain aspects, once S.ISR is released from S.ESR, after cleavage by P.ESR, signal is generated by the separation of the fluorophore-quencher pair. Here, FAM is used as the fluorophore and a Blackhole Quencher is used to quench the FAM molecule. However, any fluor-quencher pair can be used. The released S.ISR is referred to as S.Waste because it is the waste product of the reaction Since it does not participate further. However, because the S.Waste sequence is still homologous to S.ESR, it can inhibit the reaction by hybridizing to released S.ESRs. Therefore, it is a good practice to design S.Waste such that it becomes an inert hairpin after release from S.ESR. The appropriate S.Waste melt temperature is above the pre-cleavage S.ISR melt temperature but below the S.ISR post-cleavage melt temperature (FIG. 8).

S Sequence Catalytic Core Domain: S.CC.

Unlike the 8-17 DNAzyme, the catalytic core sequence for the 10-23 DNAzyme can be the same for all probes where S.CC is the catalytic core for the 10-23 DNAzyme encoded in the ESR. The optimal catalytic core sequence for the 10-23 DNAzyme is 5'-GGCTAGCTACAACGA-3' (SEQ ID NO:4).

S Sequence Cleavage Site Domain: S.RY.

S.RY is the cleavage site for the 10-23 DNAzyme encoded by the other probe's ESR. The cleavage site comprises an unpaired purine R with an RNA pyramidine, Y. Assisted by a divalent metal cation (e.g., $Mg^{2+}$) the 10-23 enzyme deprotonates the RNA 2' hydroxyl and the resulting 2' oxyanion attacks the neighboring phosphate to form a 2',3'-cyclic phosphate at the 3' end of the upstream product and a 5'-hydroxyl at the 5' end of the downstream product (Joyce, (2001) *Methods Enzymol.*, 341:503-17). RY affects cleavage efficiency as follows: RY=GrU≥GrC>>ArC, where the GU dinucleotide provides the highest cleavage efficiency (Cairns et al., 2003), "r" indicates ribonucleotide linkage. Because cleavage efficiency impacts amplification efficiency in DRCC, the most efficient dinucleotide, GrU, is used here.

Sequence Domains: S.1 and S.2.

S.1 and S.2 comprise the substrate arms of the 10-23 DNAzyme encoded in S.ESR. The sequences also form the landing site for P.ESR. Unlike S.2, S.1 must be duplicated so that one S.1 sequence acts as the DNAzyme substrate arm and the other flanks RY to provide a landing site for P.ESR.

Sequence Domain: S.Y.

S.Y is the base at the 3' end of the S.1 DNAzyme substrate arm. S.Y can be considered part of S.1 but the sequence is determined, not by S.ESR hybridization thermodynamics, like the rest of S.1, but by selection of P.Y, the pyramidine ribonucleotide to which it binds on P. Because P.RY=GU, S.Y=A. Like S.1, this base is duplicated again to provide the landing site for P.ESR.

Probe Sequence Domain: S.5.

Between the complementary probe's DNAzyme (ESR) landing site and the probe stem, a 10-base spacer can be inserted to ensure sufficient conformational flexibility in the loop for intermolecular hybridization with the DNAzyme without disrupting the stem structure.

Probe Sequence Domains: S.(1[1:6]) and S.6'.

Together, these two sequence regions comprise the probe's Inhibiting Sequence Region (S.ISR). S.6 and S.6' allow the binding energy of S.ESR to be adjusted without affecting S.ESR, greatly simplifying the design. S.(1'[1:6]) is the portion of ISR that is complementary to the first six bases in S.1 (S.1[1:6]). Binding to S.1[1:6] effectively deactivates S.ESR (1/CC/2) because S.1 is not free to bind R.1'.

Probe P Sequence Domains.

Probe P probe sequence is dictated entirely by Probe S. The probe encodes a 10-23 DNAzyme, where P.1' and P.2' act as the DNAzyme's substrate-binding arms as well as the substrate for S.ESR, along with P.RY.

Sequence Domain Notation.

Domain abstraction simplifies the sequence design process for hybridization-based DNA circuits. Sequence domains are represented by Arabic numerals (FIG. 11). Numerals with a prime (') denote domains complementary to the domains represented by the same numeral (e.g., 1' is a sequence domain that is complementary to sequence domain 1). Single-stranded molecules of DNA (strands) consist of one or more concatenated domains and are represented by capital English letters (see FIG. 11). The same domain (sequence) and its complement will usually reside on multiple strands. Domains are therefore usually referenced as a subset of their parent strand using decimal notation. For example, A.1 refers to sequence domain 1 on strand A in FIG. 11, which is GGTTT. If multiple domains are being referenced, they are concatenated using commas in order from the 5' end to the 3' end of the parent strand. For example, A.1,2 refers to sequence GGTTTTCTGA in FIG. 12 formed by domains 1 and 2 on parent strand A in FIG. 12 whereby domain 1 is located at the 5' end of domain 2.

Nucleotide Array Notation.

Individual nucleotides or series of nucleotides within a DNA strand can be addressed by its location within its parent strand or sequence domain using array notation. All nucleotide base addresses are indexed from the 5' end. Take the sequence in FIG. 12, for example, A[1] refers to the first base in the strand counting from the 5' end which is a G. Sequence domains can also be indexed. Using the sequence in FIG. 12, the following examples show how array notation is used: (i) A=GGTTTTCTGA=Strand A, (ii) A.1=GGTTT (Sequence Domain 1 on Strand A), (iii) A[1]=G (first base in Strand A), (iv) A.1[1]=G (the first base in Sequence Domain 1 on strand A), (v) A[1:4] or A[:4]=GGTT (bases 1 through 4 in Strand A), and (vi) A.1[2:]=GTTT (bases 2 through the last base in Sequence Domain 1 in Strand A).

Sequence Domain Notation.

A stretch of several consecutive nucleotides must be complementary in order for the bound state to exist as an intermediate for further reaction at longer time scales. One useful abstraction for understanding hybridization-based constructions that exploit such intermediates is the sequence domain, a consecutive stretch of nucleotides designed to act as a sequence unit.

DNA complexes can comprise several strands bound noncovalently to each other and are also represented by the concatenated letters of the constituent strands. If strand M binds to T, for example, the resultant complex is MT.

Target Recognition Integrated into DRCC Ping-Pong Probe.

Figure 14:
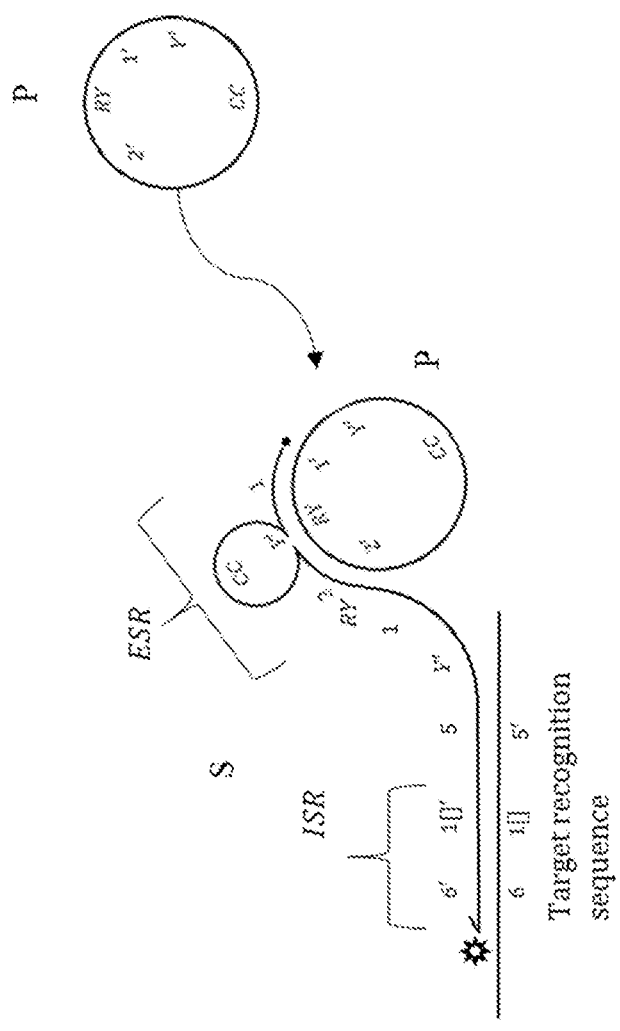
FIG. 14 illustrates the probe complex shown in FIG. 13 with the constituent strands also depicted.
Figure 14:
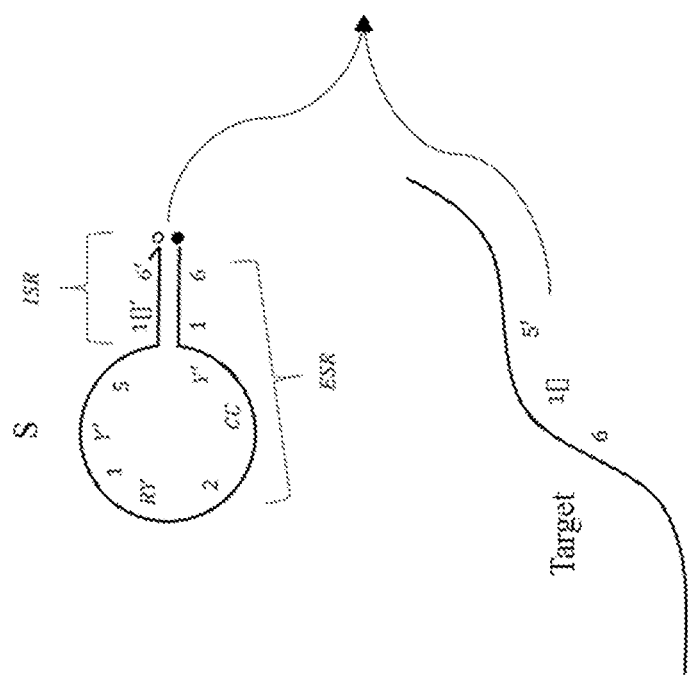

Target recognition may be integrated into the DRCC Ping-pong probe (Probe S). In this case, the all or part of sequence domain 5 on Probe S is designed to be homologous to the target recognition site, along with the entire ISR sequence adjacent to sequence domain 5 (regions S.1' and S.6'), as shown in FIG. 13, FIG. 14, and FIG. 15.

Toehold-Mediated Strand-Displacement.

Figures 15, 16:
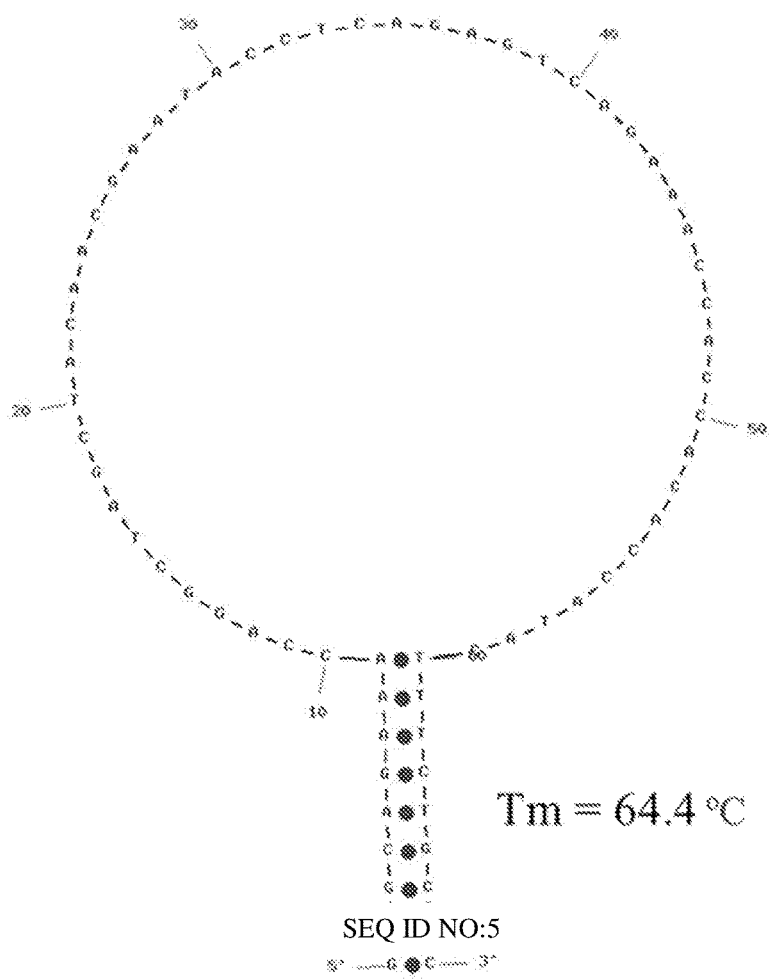
FIG. 15 illustrates a linear depiction of an allosteric functional nucleic-acid probe (AFNAP) design integrated into DRCC (target binding activates enzymatic activity).
FIG. 16 illustrates a unifold simulation of the probe design shown in FIG. 15. The hairpin stem Tm (ISR) is 64.4° C.

Initially, Probe S binds to the target exclusively through sequence region 5 which is exposed within the loop region of the probe (see FIG. 15). It's important that the melt temperature (Tm) of S.5-target duplex is well above the reaction temperature so that the target is stably bound to the loop hairpin. In the design shown in FIG. 15, the S.5-target Tm is 68.6° C., well above the reaction temperature of 37° C.

This probe is designed to bind to the target sequence shown in FIG. 15 which represents a 22-base miRNA strand. Once the target sequence binds to S.5, the target begins to displace S.6 and S.1 from the ISR using toe-hold mediated strand displacement. The competing interactions among strands are entirely determined by domain complementarities rather than Tm and the exact sequences of the domains have relatively little impact on the binding properties of the strands, except insofar as poor sequence design could lead to spurious binding between noncomplementary domains (Zhang et al., (2010) *J. Am. Chem. Soc.*, 131:17303-14). This sequence flexibility allows many instances of hybridization-based target recognition sequences.

Figure 17:
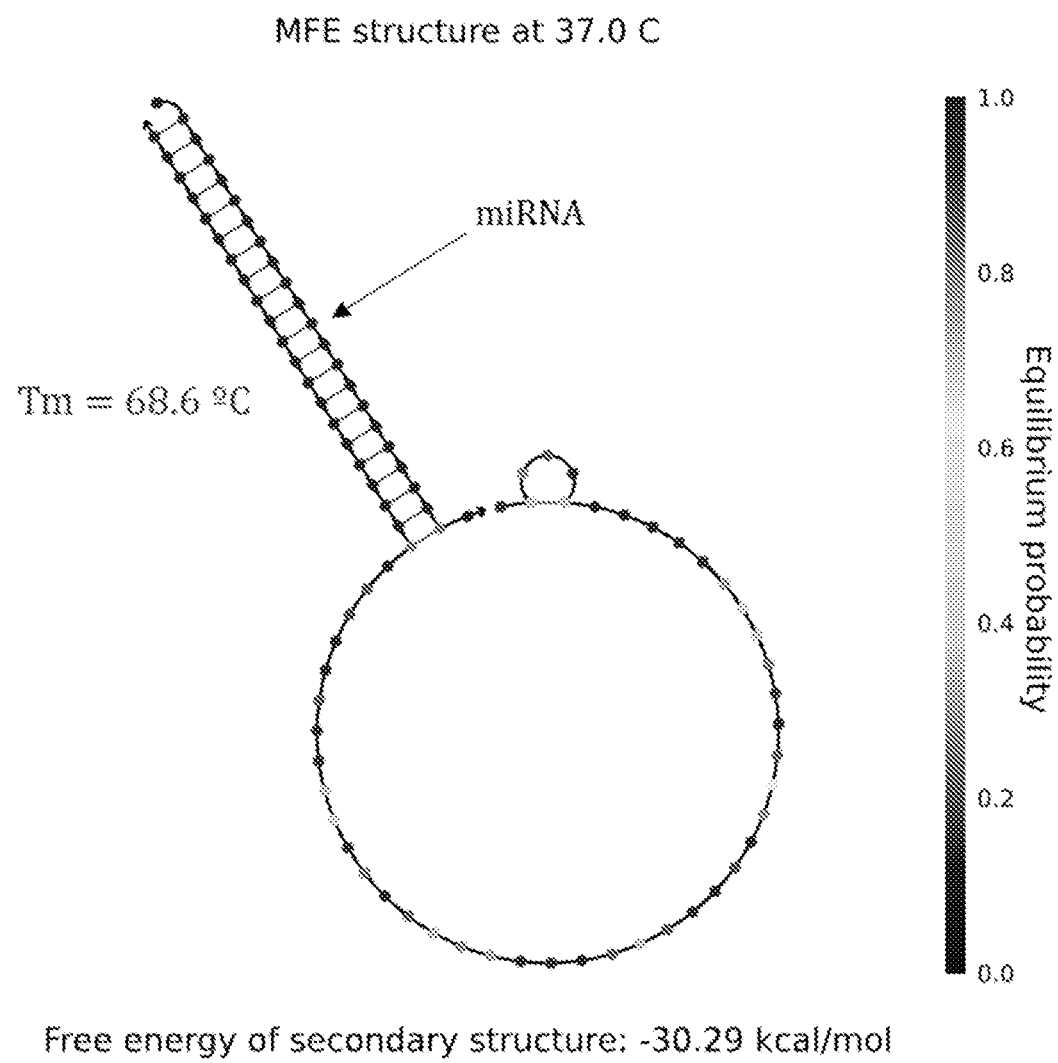
FIG. 17 illustrates a NUPACK simulation of the probe-target sequences displayed in FIG. 15. The simulation included 200 nM of probe with 1 nM of target. NUPACK showed all 1 nM of target bounded to the probe at equilibrium due to toehold mediated strand displacement.

Because the target is bound firmly to S.5, it can be outcompeted by S.1 (with S.6) without denaturing from Probe S. However, if the target strand stochastically (randomly) progresses far enough into S.1', the stem will denature permanently as the target is free to bind to the rest of S.1' and S.6'. Unlike the target, the stem has no toehold that it can use to work its way back against the target. This stability asymmetry ensures that the target will win the competition for the S.1 and S.6'. FIG. 17 displays a NUPACK simulation for the probe-target sequences shown in FIG. 15.

Figure 18:
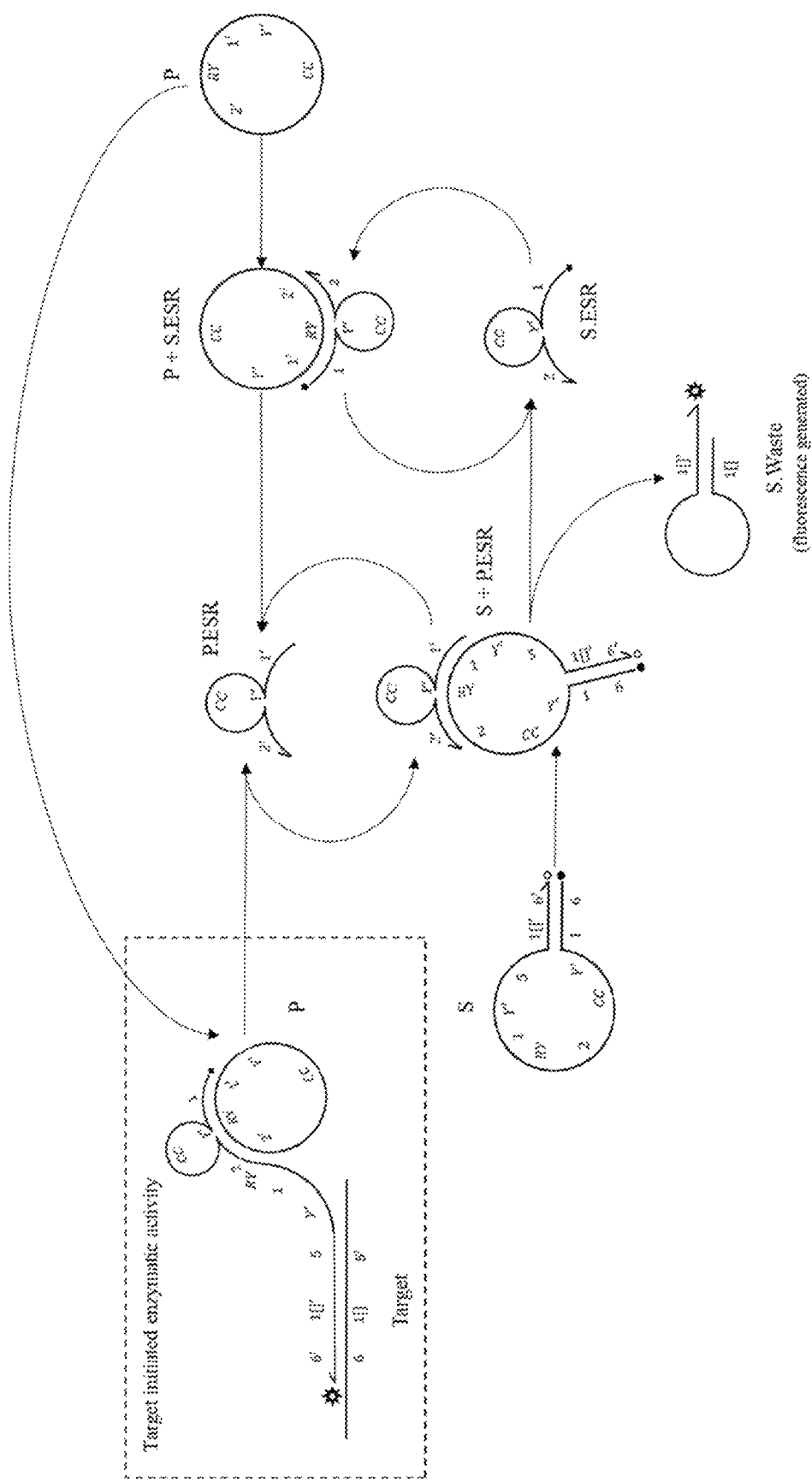
FIG. 18 illustrates DRCC with target-initiated enzymatic activity.

Once bound to regions S.1' and S.6', which comprise the probe's ISR, the ESR's substrate encoded by sequence region S.1 is liberated, freeing the ESR to catalyze substrate probes (Probe R). Thus target-specific binding activates the probe's enzymatic activity upon binding to a target analyte and, once activated, the activated probe is free to continuously cleave the complementary Ping Pong probe specie (the presence of a target analyte triggers continuous catalysis within the same probe). The entire target-initiated DRCC reaction is shown in FIG. 18.

Protein Detection.

By encoding an aptamer in the target recognition sequence, DRCC can be also be used to detect a target protein. While it is possible to simply replace the allosteric site in FIG. 15 with an aptamer sequence that binds to a specific protein, the aptamer design is more complex and it can be advantageous to add a third probe to the DRCC reaction for target recognition that does not participate in the exponential "ping pong" reaction.

Figure 19:
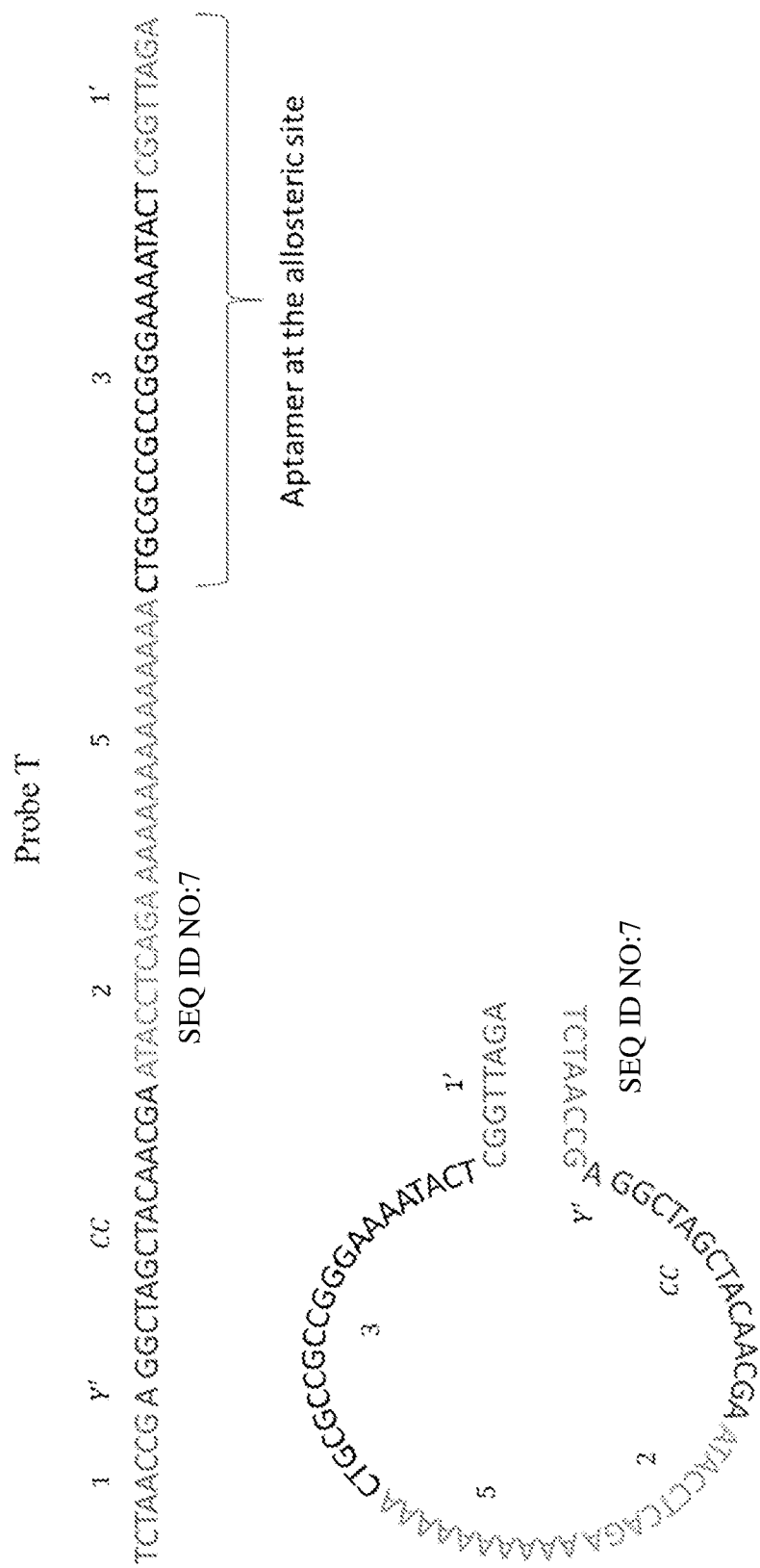
FIG. 19 illustrates a target recognition probe, activated up binding to the protein tyrosine kinase-7, a protein associated with a number of cancers.

In this case, because the target recognition probe is not cleaved by the complementary probe's ESR, it does not need to include a landing and cleavage site for the complementary probe. FIG. 19 shows a sequence design for target recognition probe T. Probe T follows the general AFNAP design concept where is activated when target-binding liberates the ESR from the ISR.

Together, sequences T.3 and T.1' encode an aptamer that binds specifically to the protein tyrosine kinase-7 (PTK7), a protein associated with a number of cancers (Shi et al., (2011) *PNAS*, 108(10):3900). Similarly to the nucleic-acid sensing probe in FIG. 15, when Probe T encounters its target protein, the exposed target recognition site sequence, T.3, will bind to the target protein and eventually wrestle T.1' away from T.1 and thus activating the DNAzyme encoded by regions T.1, T.Y', T.CC, and T.2. A spacer can be provided between the aptamer sequence, T.3. and the DNAzyme sequence T.2, in order to give the enzyme conformational freedom to bind and cleavage substrate while the allosteric site is bound to target.

In certain aspects of the invention, the FNAP is the AFNAP having a cleavage site in the hairpin-loop, and whose substrate is the cleavage-activated catalytic substrate (CACS). In this embodiment, the AFNAP is activated by target-binding but can also be activated by an activated CACS. In the presence of target, therefore, the deoxyribozyme ribonuclease cleavage cascade (DRCC) can be initiated by a single AFNAP target-binding event because the AFNAP activates many CACSs which, in turn, activate many other AFNAPs and so on and so forth, resulting in an exponential cleavage cascade. In a related embodiment, the AFNAP may be labelled with a fluor and a quencher so that every cleavage event produces an optical signal.

In further embodiments, the FNAP is not an AFNAP but simply an aptamer and NAE on the same strand whereby the NAE is always active rather than allosterically activated. This method requires that incubation of the FNAPs occurs prior to portioning because a wash step is required to remove unbound probes, thus delaying the time to signal concentration within a droplet because an signal generated in bulk suspension will be diluted. In a related embodiment, an antibody may be substituted for the aptamer resulting in an NAE-conjugated antibody. Because direct conjugation between nucleic acids and antibodies can be problematic, the antibody can be conjugated to streptavidin and hybridized to a biotinylated NEA prior to incubation with the test sample. An example of a method for performing the wash step employs a semi-permeable membrane to catch target cells but allow unbound probes to pass through. Another exemplary method uses paramagnetic microspheres to bind target cells which are pulled down in the presence of a magnet and the suspension is replaced.

In certain embodiments, there is a two-step allosteric activation of the AFNAP. In this embodiment, an allosteric binding site probe (ABSP) binds to the target analyte and, upon binding, exposes the nucleic acid target binding site that activates an AFNAP when it binds to the ABSP. The advantage of using this method is that all AFNAP thermodynamics are governed by nucleic acid thermodynamics, decoupling the probe switching mechanism from aptamer thermodynamics. While the ABSP does depend on aptamer thermodynamics, it is a much simpler probe and, therefore, easier to select through selective pressure (multi-step SELEX). The method also enables the use of universal AFNAP probes since it is possible that the only target-specific portion of the concept lies in the ABSP. Therefore, only ABSP design would need to change for different assays. In a similar embodiment, the ABSP could be used to activate an MNAzyme rather than a AFNAP. In this embodiment, the binding of the ASR in the ABSP exposes the landing site for one or both partzymes which comprise an MNAzyme and thus activating catalysis in the presence of the target analyte.

It should be noted that the nucleic-acid activated AFNAP can be used to detect target nucleic acids from cells or viruses within droplets or in a bulk reaction. When employed within the DRCC this method offers the ability to detect target nucleic acids quickly and inexpensively at a single reaction temperature and, thus, could be used for digital quantification of nucleic acids.

Thus, using DRCC, AFNAPs may be used for comprehensive cell analysis. AFNAPs can be used to identify surface biomarkers and secreted biomarkers for an isolated cell within a droplet. This is particularly useful in cancer diagnosis since secreted miRNAs can be tumor specific and play a role as signaling molecules to the establishment and maintenance of the tumor microenvironment. Thus they could be used in combination with surface proteins and other secreted biomarkers to predict treatment response and to detect tumorigenesis. If cancer drugs are introduced into the analysis reagents and the comprehensive cellular response can also be characterized beyond identification and viability.

In any of the above embodiments, a linker can be used between the recognition element and the enzymatic domain of the FNAP. The reason for the linker would be if direct conjugation to the surface recognition element does not provide enough "flexibility" for the NAE to catalyze substrate efficiently with the probe is bound to the cell surface. Similarly, a linker may be introduced into the CACS described above in order to facilitate AFNAP access to the cleavage site.

The methods of the invention do not preclude the use of any type of nucleic acid or nucleic acid modification. The selection of nucleic acid and/or which modifications to include depend on the conditions within the test sample. All of the oligonucleotides described herein are often chimeric and can comprise DNA, RNA, PNA, L-DNA or L-RNA depending on the design best suited to the application. The method does not exclude modifications including but not limited to inverted thymidine at the 3' end and or 2'-O-methyl modification that increase stability in physiological conditions, for example.

B. Test Sample

Target cells in the test sample include bacteria, fungi, plant cells, animal cells, or cells from any other cellular organism. The cells may be cultured cells or cells obtained directly from naturally occurring sources. The cells may be obtained directly from an organism or from a biological sample obtained from an organism, e.g., from sputum, saliva, urine, blood, cerebrospinal fluid, seminal fluid, stool, and tissue. Any tissue or body fluid specimen.

In one embodiment the test sample includes cells that are isolated from a biological sample comprising a variety of other components, such as non-target cells (background cells), viruses, proteins, and cell-free nucleic acids. The cells may be infected with a virus or another intracellular pathogen. The isolated cells may then be re-suspended in different media than those from which they were obtained. In one embodiment the test sample comprises cells re-suspended in a nutrient medium that enables them to replicate and/or remain viable. The nutrient media may be defined media with known quantities or all ingredients or an undefined media where the nutrients are with complex ingredients such yeast extract or casein hydrolysate, which contain a mixture of many chemical species of unknown proportions, including a carbon source such as glucose, water, various salts, amino acids, and nitrogen. In a one embodiment, the target cells in the test sample comprise bacteria and the nutrient media comprises a commonly used nutrient broth (liquid media) for culturing bacteria such as Lysogeny Broth (LB broth) or Trypticase Soya Agar. In any embodiment the media may be supplemented with a blood serum or synthetic serum to facilitate the growth of fastidious organisms. In one embodiment, the target cells are human cells and the nutrient media may also comprise hormones or growth factors. The nutrient media may also be selected to inhibit or promote the growth of certain cells.

Test samples can also contain target analytes including, but not limited to, alcohol, glucose, ketones, cancer markers (e.g., prostate-specific antigen [PSA], epidermal growth factor receptor [EGFR], cancer antigen CA 15-3), cortisol, serotonin, 5-hydroxytryptophane, methadone, cocaine, cannabinoids (e.g., 11-carboxy-Δ9-tetrahydocannabinolic acid), opiates, caffeine, phenytoin, primidone, carbamazepine, antibodies, melatonin, insulin, DHEA sulfate, aldosterone, testosterone, progesterone, andostenedione, estriol, estrone, urea, uric acid, ammonia, calcium, cholesterol, lactoferrin, growth factors (e.g., EGF, NGF, IGF-1), haliperidol, theophylline, cotinine, estradiol, salicyclic acid, acetaminophen, nitrazepam, clobazam, amphetamine, quinine, lithium, antibiotics (e.g., penicillin and tetracycline), vitamins, minerals, toxins, anti-oxidants, monosodium glutamate (MSG), components of food products (e.g., peanuts and/or tree nuts), proteins and nucleic acids (e.g., DNA and RNA), including host and non-host (e.g., pathogenic) proteins and nucleic acids.

C. Analysis Reagents

Analysis reagents are the reagents used to characterize the target cell. Methods of the invention for characterizing a target cell comprise identifying the target cell, identifying attributes of the target cell, determining the viability of the target cell, and characterizing the response of a target cell to environmental stresses. In all the embodiments described herein, the analysis reagents comprise functional nucleic acids (FNAs) and constituents for enabling the use thereof, including substrates, buffers, salts, and co-factors. In one embodiment, the analysis reagents also comprise cell viability reagents which are used to characterize the viability of any cell in the test sample, including but not limited to the cells specifically targeted by the FNAs. In a related embodiment, environmental stressors are included as part of the analysis reagent. Examples of environmental stressors include antimicrobials and drugs used to treat cancer.

D. Multiplexing

The methods described herein include the specific identification of multiple target analytes from a single test sample. Analytes include target cells, surface biomarkers, and secreted biomarkers. Examples of surface biomarkers include surface proteins, surface antigens, peptides, polysaccharides, and lipids. Examples of secreted biomarkers include miRNAs, toxins, proteins, and peptides. The methods of the invention include the specific identification of multiple analytes from a single test sample.

The methods of the invention involve combining a plurality of AFNAPs with different combinations of ASRs and ESRs in order to encode multiple target cells present in a test sample. In one embodiment, each ASR is represented by a different ESR, and each ESR-specific substrate is represented by a different fluorophore. When the target cell is detected by the ASR, the NAE encoded in the ESR cleaves a substrate that releases a specific wavelength representing that cell. Thus the fluorescence dye encodes for the target cell. In another embodiment, multiple ASRs can be encoded by a single ESR so that groups of analytes are encoded by a single fluorescence channel. Thus the fluorescence dye encodes for groups of target cells. In another embodiment, combinations of ESRs and ASR are used to identify more analytes than there are fluorescent channels. Thus, one or more fluorescence dyes can be used to encode a cell and because single cell types are isolated within a droplet, two or more dye combinations can be also used to identify target cells using binary encoding, thus expanding the multiplex capability beyond the total number of dyes used (digital representation).

In a related embodiment, the hairpin-stem of the probe substrate can be designed to denature at different temperatures and the reaction can be monitored during a temperature sweep to identify which probes were cleaved. A cleaved substrate will result in a smaller change in fluorescence over its designated melt temperature compared to the other probes. This method enables the number of analytes to exceed the number of fluorescence channels and can also be employed similarly to the endpoint multiplexing schemes. It can also be used in DRCC since the CACS is also a hairpin.

E. Compartmentalization

The methods of the invention can involve combining a test sample comprising at least one target cell with analysis reagent and then partitioning the test sample into microdroplets such that droplet will typically contain one target cell. The number of droplets can vary from thousands to millions depending on the application and droplet volumes can also vary between 1 pL to 1 nL depending on the application. The methods described herein are compatible with any droplet generation method. While the methods for droplet formation differ, all the methods disperse an aqueous phase, the test sample in this case, into an immiscible phase, also referred to as the continuous phase, so that each droplet is surrounded by an immiscible carrier fluid. In one embodiment the immiscible phase is an oil wherein the oil comprises a surfactant. In a related embodiment, the immiscible phase is a fluorocarbon oil comprising a fluorosurfactant. An important advantage to using a fluorocarbon oil is that it is able to dissolve gases relatively well. Thus, the fluorocarbon oil used in the methods described herein comprises solubilized gases necessary for cell viability.

F. Signal Detection

Once a sample has been processed, e.g., droplets have been generated, they must be presented for analysis by an optical system. In one embodiment, droplets are presented in a two-dimensional array so that good thermal control can be maintained. In the droplets containing target cells, the analysis reagents will produce a concentrated fluorescent signal that will rise above the background noise. Fluorescence is detected using a camera with excitation and emission filters. One advantage of using an imaging concept rather than the more commonly used cytometry concept is that a reaction can be monitored over time rather than simply being an endpoint reaction because the array is static and can be imaged multiple times. Another advantage is that the sample or all the droplets experience the same reaction conditions at the time of analysis. With a cytometry approach, droplets pass by the detector at different times. Therefore, some droplets are incubated longer than others at the time of analysis.

Reaction Conditions.

Reaction conditions can be optimized for a particular sample, probe, or combination of probes. Reactions of the invention can be performed at temperatures of 5, 10, 15, 20, 25, 30, 35, 40, 45, 50, 55, 60, 65, 70, 75, 80, 85, to 90° C., including all values as ranges there between. In certain aspects the reaction can be performed at 25 to 45° C. A reaction can be equilibrated to a preset temperature (e.g., 70° C.) in an appropriate buffer, for example 50 mM Tris, pH 8.0, 0.1% SDS. The reaction mixture can be brought to temperature (e.g., 23° C.) before initiation of the reaction. In certain aspects $MgCl_2$ can be added to the reaction mixture prior to compartmentalization. In certain aspects the $MgCl_2$ concentration ranges from 1 mM, 2, mM, 10 mM, 25 mM, 50 mM, 100 mM, including all ranges and values there between. NaCl can also be included in a reaction mixture. NaCl concentration can vary between 10, 25, 50 mM to 75, 100, 150 mM, including all values and ranges there between.

Probes can be present in a compartment or droplet at a concentration between 1, 10, 100 pM to 0.1, 1, 10 µM. In certain aspect the probes can be present in a concentration ranges of between 1, 10, 50 nM to 75, 100, 150, 200 nM. The probes can be assayed in a reaction having a pH between 6 to 9. In certain aspects the pH of an assay or reaction is between pH 7 and 7.5. The pH can be adjusted to optimize the enzymatic activity of a probe, with higher pH assisting with deprotonating the RNA 2' hydroxyl.

G. Cell Viability

Analysis reagents can also include cell viability reagents. Combined with an environment stressor, a cell viability assay can be used to determine whether or not a cell is susceptible to the environmental stressor. In one embodiment, an antimicrobial drug is included in the analysis reagents. When the test sample is partitioned into droplets, the isolated bacteria within the droplet will generate a signal at a fluorescence wavelength emitted by the viability reagents and the signal can be associated with their response to the antibiotic. Over a given period of time, bacteria that are resistant to the antimicrobial included in the analysis reagents will produce a brighter fluorescent signal than those that are susceptible to the antimicrobial. The methods of the invention described above will identify the bacteria species so that, combined with the viability assessment, an accurate phenotypic drug resistance profile is ascertained for the population of target cells present in the test sample. In a related embodiment, the target cells are cancer cells and the environmental stressor is a cancer drug.

The methods of the invention are compatible with any viability reagent that does not require cell lysis. In one embodiment the viability reagent is resazurin-based. In a viable cell, resazurin is reduced into resorufin, which is highly fluorescent, in the bacteria's cytosol and then secreted into the droplet. The limited-diffusion confinement of secreted resorufin quickly concentrates to detectable signal levels and the detected by the methods described above. Examples of resazurin-based reagents are AlamarBlue (various), PrestoBlue (Thermo Fisher Scientific), CelltiterBlue (Promega), Resazurin sodium salt powder. In an alternate embodiment, tetrazolium-reduction, can be used as the cell viability indicator. Examples include MTT, XTT, and the WST series. In an alternate embodiment, protease markers can be used to determine cell viability.

What is claimed is:

1. A nucleic acid probe composition comprising a first functional nucleic acid probe comprising:
   a first end coupled to a quencher or a fluorophore, wherein the quencher or fluorophore is coupled directly to the first end or is coupled to the first end by a first terminal linker;
   a second end coupled to a fluorophore or a quencher, wherein the quencher or fluorophore is coupled directly to the second end or is coupled to the second end by a second terminal linker; and
   from the first end to the second end:
   (a) a first substrate recognition sequence;
   (b) a first catalytic core sequence;
   (c) a second substrate recognition sequence that is also operable as a landing sequence for an enzymatic sequence;

(d) a cleavage site that can be cleaved by the enzymatic sequence;
(e) a second landing sequence for the enzymatic sequence;
(f) a linker comprising a target binding region or a spacer region comprising a target binding region; and
(g) a first inhibitory sequence that is complementary to all or some of the first substrate recognition sequence;
wherein (1) the first inhibitory sequence or (2) the first inhibitory sequence and the second terminal linker sequesters the first substrate recognition sequence when the cleavage site is uncleaved.

2. The composition of claim 1, wherein the first substrate recognition sequence, the first catalytic core sequence, and the second substrate recognition sequence form a nucleic acid enzyme (NAE).

3. The composition of claim 2, wherein the NAE is a 10-23 DNAzyme, an 8-17 DNAzyme, or a G-quadruplex DNAzyme.

4. The composition of claim 1, wherein the target binding region comprises an aptamer.

5. The composition of claim 1, further comprising a second functional nucleic acid probe comprising:
a first end coupled to a quencher or a fluorophore, wherein the quencher or fluorophore is coupled directly to the first end or is coupled to the first end by a first terminal linker; and
from the first end to a second end of the second functional nucleic acid probe:
(i) first substrate recognition sequence;
(ii) a catalytic core sequence;
(iii) a second substrate recognition sequence that is also operable as a landing sequence for an enzymatic sequence; and
(iv) a cleavage site that can be cleaved by the enzymatic sequence of (iii).

6. A method for analyzing target analytes, comprising:
(a) providing a plurality of partitions with at least one partition comprising at least one target analyte, a first functional nucleic acid probe of claim 1, an oligonucleotide probe substrate, and constituents required for analyte binding, substrate binding, and substrate catalysis;
(b) incubating the partitions with the first functional nucleic acid probe, probe substrate, and constituents wherein at least one probe binds to the target analyte;
(c) activating a nucleic acid enzyme within the first functional nucleic acid probe that continuously catalyzes a reaction throughout the incubation, whereby the product of the reaction releases a detectable label;
(d) producing an accumulation of detectable label within the partition; and
(e) detecting the detectable label.

7. The method of claim 6, wherein the partitions comprise droplets in an immiscible fluid.

8. The method of claim 7, wherein the droplets are arranged in a static two-dimensional array monolayer for incubation and detection.

9. The method of claim 8, wherein the immiscible fluid is a fluorocarbon comprising a fluorosurfactant.

10. The method of claim 8, wherein the droplet partitions are generated using Laplace pressure gradients or shear stress.

11. The method of claim 8, wherein detection is performed using a camera comprising a plurality of emission filters and magnifications or a plurality of light emitting diodes (LEDs) combined with a plurality of excitation filters.

12. The method of claim 6, wherein the nucleic acid enzyme is an endonuclease.

13. The method of claim 12, wherein the oligonucleotide probe substrate is labeled with a fluorophore and a quencher wherein the fluorophore is separated from the quencher after endonucleatic cleavage.

14. The method of claim 13, wherein the oligonucleotide probe substrate is a stem-loop structure.

15. The method of claim 12, wherein the first functional nucleic acid probe comprises an aptazyme, or an allosteric aptazyme.

16. The method of claim 12, wherein the nucleic acid enzyme is a 10-23 DNAzyme or derivative thereof, or an 8-17 DNAzyme or derivative thereof, or a G-quadruplex DNAzyme or derivative thereof.

17. The method of claim 6, wherein the partitions further comprise an environmental stressor.

18. The method of claim 17, wherein the environmental stressor is an antimicrobial.

19. The method of claim 6, wherein the oligonucleotide probe substrate is a cleavage-activated catalytic substrate comprising a nucleic acid enzyme encoded within an enzymatic sequence region that is partially bound to an inhibiting sequence region and when the substrate is cleaved, the inhibiting sequence region is severed from the enzymatic sequence region, liberating the nucleic acid enzyme encoded within the enzymatic sequence region.

20. The method of claim 19, wherein an allosteric sequence region in the at least one probe binds to the target analyte, and wherein an exponential deoxyribozyme ribonuclease cleavage cascade is initiated by the liberated nucleic acid enzyme, wherein the liberated nucleic acid enzyme:
(a) binds to a loop region of the first functional nucleic acid probe; and
(b) catalyzes the cleavage of the first functional nucleic acid probe, bypassing the allosteric sequence region by severing the inhibiting sequence region from the enzymatic sequence region.

* * * * *

UNITED STATES PATENT AND TRADEMARK OFFICE
CERTIFICATE OF CORRECTION

| | |
|---|---|
| PATENT NO. | : 11,268,135 B2 |
| APPLICATION NO. | : 16/300469 |
| DATED | : March 8, 2022 |
| INVENTOR(S) | : Arab |

It is certified that error appears in the above-identified patent and that said Letters Patent is hereby corrected as shown below:

In the Claims

Claim 5, Column 27, Line 32: please insert --a-- before the word first, at the beginning of element (i).

Signed and Sealed this
Eighth Day of November, 2022

Katherine Kelly Vidal
*Director of the United States Patent and Trademark Office*